(12) United States Patent
Hamano et al.

(10) Patent No.: US 9,855,018 B2
(45) Date of Patent: Jan. 2, 2018

(54) DIAGNOSTIC MEDICAL IMAGE SYSTEM AND METHOD OF INTRODUCING TALBOT CAPTURING DEVICE TO DIAGNOSTIC MEDICAL IMAGE SYSTEM USED FOR GENERAL CAPTURING

(71) Applicant: Konica Minolta, Inc., Chiyoda-ku, Tokyo (JP)

(72) Inventors: Masaya Hamano, Tokyo (JP); Akira Kurahashi, Hachioji (JP); Norihiro Matsusaka, Hino (JP); Junko Kiyohara, Hino (JP); Tomoyasu Yokoyama, Tsurugashima (JP); Satoshi Nishino, Sayama (JP)

(73) Assignee: KONICA MINOLTA, INC., Tokyo (JP)

( * ) Notice: Subject to any disclaimer, the term of this patent is extended or adjusted under 35 U.S.C. 154(b) by 260 days.

(21) Appl. No.: 14/782,968

(22) PCT Filed: Feb. 25, 2014

(86) PCT No.: PCT/JP2014/054514
§ 371 (c)(1),
(2) Date: Oct. 7, 2015

(87) PCT Pub. No.: WO2014/167901
PCT Pub. Date: Oct. 16, 2014

(65) Prior Publication Data
US 2016/0310099 A1    Oct. 27, 2016

(30) Foreign Application Priority Data

Apr. 8, 2013 (JP) .................................. 2013-080273
Dec. 12, 2013 (JP) .................................. 2013-256561

(51) Int. Cl.
*A61B 6/00* (2006.01)
*A61B 6/04* (2006.01)

(52) U.S. Cl.
CPC ............ *A61B 6/566* (2013.01); *A61B 6/4035* (2013.01); *A61B 6/4233* (2013.01);
(Continued)

(58) Field of Classification Search
CPC ................................ A61B 6/563; A61B 6/566
See application file for complete search history.

(56) References Cited

U.S. PATENT DOCUMENTS

2011/0317809 A1* 12/2011 Eguchi ................. A61B 6/4233
378/62
2013/0011040 A1* 1/2013 Kido .................... A61B 6/4291
382/132

FOREIGN PATENT DOCUMENTS

JP    2008200357 A    9/2008
JP    2008200359 A    9/2008
(Continued)

OTHER PUBLICATIONS

International Preliminary Report on Patentability corresponding to Application No. PCT/JP2014/054514; dated Oct. 13, 2015, with English translation.
(Continued)

*Primary Examiner* — Dani Fox
(74) *Attorney, Agent, or Firm* — Cantor Colburn LLP

(57) ABSTRACT

Provided are a diagnostic medical image system and the like which enable diagnostic medical images generated in either an imaging system used for general imaging or an imaging system which includes a Talbot imaging device to be accurately associated with imaging order information. In the diagnostic medical image system, a controller groups a plurality of types of diagnostic medical images recon-
(Continued)

structed and generated on the basis of a plurality of image signals captured by a second imaging system equipped with a Talbot imaging device and transmits the group to a console; and the console associates one diagnostic medical image generated from one image signal acquired from a first imaging system equipped with an X-ray imaging device with the imaging order information corresponding thereto and, by the same associating method, associates the grouped plurality of types of diagnostic medical images transmitted from the controller with the imaging order information corresponding thereto.

15 Claims, 17 Drawing Sheets

(52) U.S. Cl.
CPC .......... *A61B 6/4266* (2013.01); *A61B 6/4283* (2013.01); *A61B 6/4417* (2013.01); *A61B 6/463* (2013.01); *A61B 6/483* (2013.01); *A61B 6/484* (2013.01); *A61B 6/5235* (2013.01); *A61B 6/5247* (2013.01); *A61B 6/563* (2013.01); *A61B 6/0407* (2013.01); *A61B 6/4452* (2013.01); *A61B 6/465* (2013.01); *A61B 6/467* (2013.01)

(56) References Cited

FOREIGN PATENT DOCUMENTS

| | | |
|---|---|---|
| JP | 2010259688 A | 11/2010 |
| JP | 2013154146 A | 8/2013 |
| JP | 2014004486 A | 1/2014 |
| WO | 2004058070 A1 | 7/2004 |
| WO | 2008102598 A1 | 8/2008 |
| WO | 2010050483 A1 | 5/2010 |
| WO | 2010073894 A1 | 7/2010 |
| WO | 2010134365 A1 | 11/2010 |
| WO | 2011033798 A1 | 3/2011 |
| WO | 2011114845 A1 | 9/2011 |
| WO | 2011142157 A1 | 11/2011 |
| WO | 2012029340 A1 | 3/2012 |

OTHER PUBLICATIONS

Written Opinion of the International Searching Authority corresponding to Application No. PCT/JP2014/054514; dated Jun. 3, 2014.
International Search Report corresponding to Application No. PCT/JP2014/054514; dated Jun. 3, 2014, with English translation.
Masabumi Nagashima et al., "Optimization of the Joint and Cartilage: Diagnostic Potential of the Differential Inferential Contrast X-ray Imaging," (14th Meeting of the Japanese Research Society of Clinical Anatomy, Feb. 2011, No. 11, pp. 56-57.

* cited by examiner

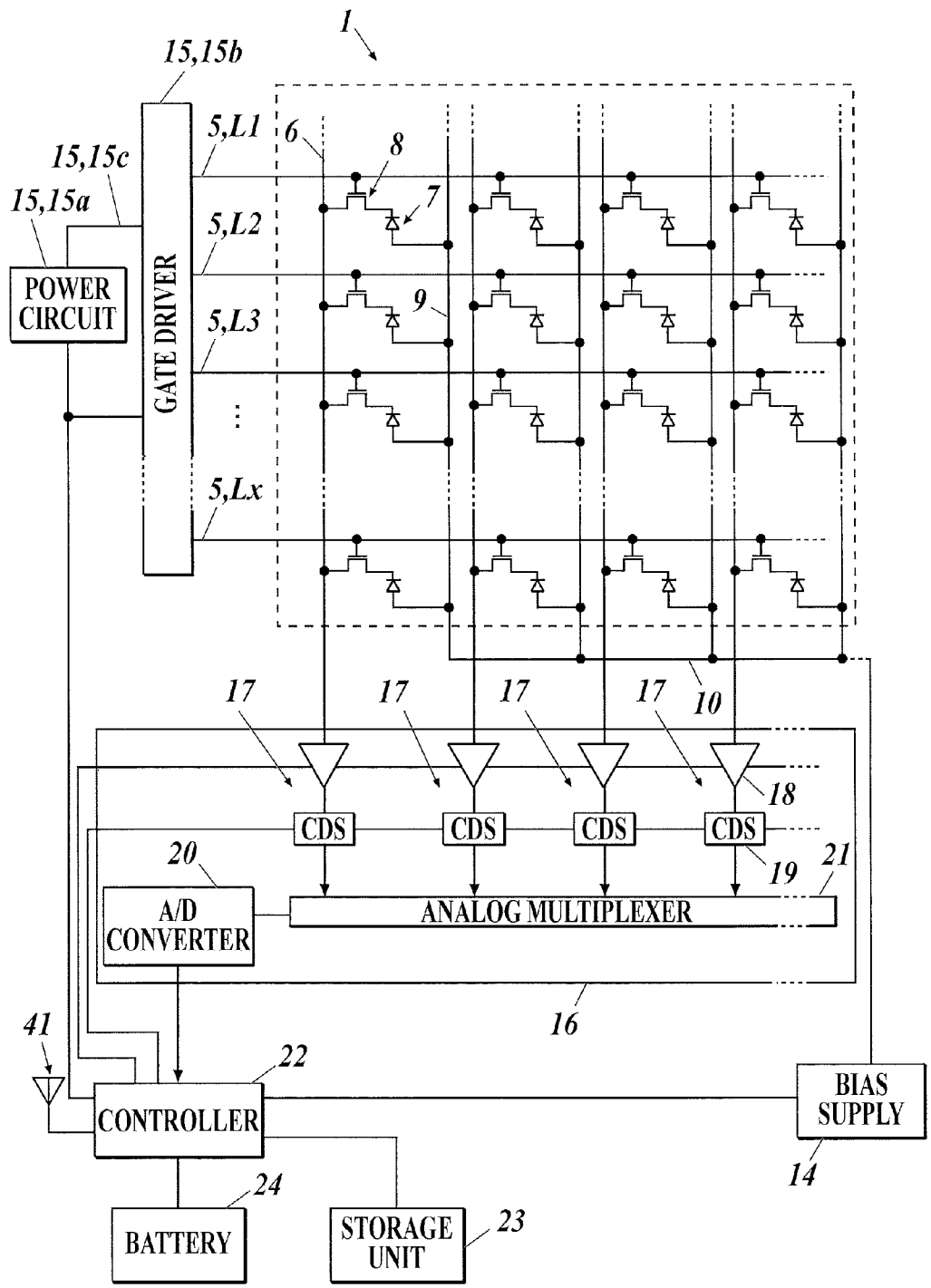

FIG.4

| CAPTURING ORDER ID | PATIENT ID | PATIENT NAME | SEX | AGE | CLINICAL DEPARTMENT NAME | CAPTURED SITE | CAPTURING DIRECTION | BUCKY DEVICE ID |
|---|---|---|---|---|---|---|---|---|
| 001 | 100085 | M | MALE | 25 | ORTHOPEDICS | ABDOMEN | FRONT P→A | 002 |
| 002 | 100085 | M | MALE | 25 | ORTHOPEDICS | CHEST | FRONT P→A | 001 |
| 003 | 100085 | M | MALE | 25 | ORTHOPEDICS | HEAD | FRONT P→A | 001 |
| 004 | 100085 | M | MALE | 25 | ORTHOPEDICS | LEG | R | 003 |
| 005 | 100063 | W | FEMALE | 32 | SURGERY | CHEST | SIDE R→L | 001 |
| 006 | 100063 | W | FEMALE | 32 | SURGERY | ABDOMEN | FRONT A→P | 002 |

P1 — CAPTURING ORDER ID
P2 — PATIENT ID
P3 — PATIENT NAME
P4 — SEX
P5 — AGE
P6 — CLINICAL DEPARTMENT NAME
P7 — CAPTURED SITE
P8 — CAPTURING DIRECTION
P9 — BUCKY DEVICE ID

FIG.5

INPUT CAPTURING ORDER INFORMATION FOR SCHEDULED CAPTURING

| CAPTURING ORDER ID | PATIENT ID | PATIENT NAME | SEX | AGE | CLINICAL DEPARTMENT NAME | CAPTURED SITE | CAPTURING DIRECTION | BUCKY DEVICE ID |
|---|---|---|---|---|---|---|---|---|
| 001 | 100085 | M | MALE | 25 | ORTHOPEDICS | ABDOMEN | FRONT P → A | 002 |
| 002 | 100085 | M | MALE | 25 | ORTHOPEDICS | CHEST | FRONT P → A | 001 |
| 003 | 100085 | M | MALE | 25 | ORTHOPEDICS | HEAD | FRONT P → A | 001 |
| 004 | 100085 | M | MALE | 25 | ORTHOPEDICS | LEG | R | 003 |

ENTER  RETURN

DIAGNOSTIC MEDICAL IMAGE SYSTEM AND METHOD OF INTRODUCING TALBOT CAPTURING DEVICE TO DIAGNOSTIC MEDICAL IMAGE SYSTEM USED FOR GENERAL CAPTURING

CROSS REFERENCE TO RELATED APPLICATIONS

This is the U.S. national stage of application No. PCT/JP2014/054514, filed on Feb. 25, 2014. Priority under 35 U.S.C. §119(a) and 35 U.S.C. §365(b) is claimed from Japanese Application No. 2013-080273, filed Apr. 8, 2013, and from Application No. 2013-0256561, filed Dec. 12, 2013, the disclosures of which are also incorporated herein by reference.

TECHNICAL FIELD

The present invention relates to a diagnostic medical image system including a first capturing unit for performing general capturing with an X-ray source and an X-ray capturing device, and a second capturing unit for capturing several types of diagnostic medical images with a Talbot capturing device.

BACKGROUND ART

In the field of X-ray capturing, the transition of X-ray capturing devices from conventional silver halide photographic devices including screens or films to CR (computed radiographic) units including photostimulable phosphor sheets has led to transition to X-ray capturing devices that capture X-ray images in the form of image signals. Various flat panel detectors (FPDs) have been developed that read electrical signals generated by a two-dimensional array of transducers, which generate electrical signals corresponding to X-ray beams irradiated from an X-ray source through a subject, as image signals. Such FPDs have been used in medical settings, e.g., hospitals, for capturing of diagnostic medical images (for example, refer to Patent Literature 1).

In X-ray capturing using an FPD, usually the FPD is irradiated once with X-ray beams from an X-ray source and passing through a subject and reads image signals corresponding to one medical image. The process of irradiating the FPD once with X-ray beams from the X-ray source and passing through the subject and capturing image signals corresponding to one medical image is referred to as general capturing. This process may also be referred to as simple capturing, which is typical X-ray capturing. Recently developed X-ray capturing devices including such FPDs further include Talbot interferometers or Talbot-Lau interferometers, which include X-ray sources for irradiation of X-ray beams onto the FPDs and a plurality of gratings (for example, refer to Patent Literatures 2 and 3). FPDs in X-ray capturing devices including Talbot or Talbot-Lau interferometers are hereinafter referred to as "X-ray detectors" in distinction from FPDs used in general capturing, but the structures of these FPDs are basically identical. X-ray capturing devices including Talbot or Talbot-Lau interferometers are hereinafter simply referred to as Talbot capturing devices.

The following Talbot capturing devices are disclosed for example. A Talbot capturing device captures multiple moire images with an X-ray detector through multiple X-ray capturing operations at variable relative positions of two one-dimensional gratings (fringe scanning), and reconstructs and generates several types of diagnostic medical images, such as X-ray absorption images, differential phase images, and small-angle scattering images, from the moire images (for example, refer to Patent Literature 4). Such method is known as Talbot method. A variation of the Talbot method described above is a Talbot-Lau method that captures multiple moire images with an X-ray detector through multiple X-ray capturing operations using a grating newly disposed near an X-ray source and moved relative to a group of other gratings, and reconstructs and generates several types of diagnostic medical images, such as differential phase images from the moire images (for example, refer to Patent Literature 5). Another capturing device includes gratings that are removable from the path of the X-ray beams irradiated from the X-ray source and is switchable between general capturing not using gratings and Talbot method (or Talbot-Lau method) using gratings (for example, refer to Patent Literature 6).

A Fourier imaging system irradiates a subject with X-ray beams once to capture one moire image through multiple two-dimensional gratings, and reconstructs and generates several types of diagnostic medical images from the moire image through Fourier transform (for example, refer to Patent Literature 7). Another type of Talbot capturing is switchable between the fringe scanning mode and Fourier transform mode through varying of the grating positions (for example, refer to Patent Literature 8).

X-ray capturing devices including Talbot or Talbot-Lau interferometers or involving Fourier transform generate moire images containing information on the subject, whereas fringe scanning generates multiple moire images through multiple X-ray irradiation operations, and Fourier transform generates one moire image for every X-ray irradiation operation. These moire images can be analyzed to reconstruct at least three types of images: an absorption image, which is similar to that obtained through normal capturing (simple capturing), a differential phase image, and a small-angle scattering image. Such images can be combined to generate a new image. X-ray capturing devices including Talbot capturing devices and X-ray capturing devices involving Fourier transform are hereinafter simply referred to as Talbot capturing devices.

It is difficult to capture an image of the cartilage portion in a joint region of a patient of interest in general capturing. Thus, for example, a large capturing device involving magnetic resonance imaging (MRI) has been used for such capturing. Such capturing involving MRI applies physical and mental stress to the patient who is the subject and causes an increase in costs. Recent research has shown that the cartilage portion in a joint region can be captured in at least a differential phase image through capturing of a dissected joint region with a Talbot capturing device (for example, refer to Non-Patent Literature 1). Research conducted by the inventors has shown that the cartilage portion in a joint region can be captured in at least a differential phase image through capturing of a non-dissected joint region of an organism with a Talbot capturing device (for details refer to Japanese Patent Application Nos. 2012-275216 and 2013-5047). Talbot capturing devices have superb functionality for capturing images of cartilage portions in joint regions, which cannot be captured through conventional general capturing; thus, Talbot capturing devices are expected to be introduced to medical facilities such as hospitals and clinics in the near future.

PRIOR ART DOCUMENT

Patent Literature

Patent Literature 1: International Publication WO 2011/142157
Patent Literature 2: Japanese Patent Application Laid-Open No. 2008-200359
Patent Literature 3: International Publication WO 2011/033798
Patent Literature 4: International Publication WO 2004/058070
Patent Literature 5: International Publication WO 2011/114845
Patent Literature 6: International Publication WO 2008/102598
Patent Literature 7: International Publication WO 2010/050483
Patent Literature 8: International Publication WO 2012/029340

Non-Patent Literature

Non-Patent Literature 1: Masabumi Nagashima, and 7 others, "Optimization of the Joint and Cartilage: Diagnostic Potential of the Differential Interferential Contrast X-ray Imaging," (14th Meeting of Japanese Research Society of Clinical Anatomy, 2010. Sep. 11), Japanese Research Society of Clinical Anatomy, February 2011, No. 11, pp. 56-57, (search date: Apr. 5, 2013), URL: http://www.jrscajp/contents/records/contents/PDF/11-PDF/p56.pdf

SUMMARY OF INVENTION

Problems to be Solved by the Invention

Unlike capturing devices involving MRI or CT (computed tomography), the Talbot capturing devices described above are not large and have similar dimensions to those of regular radiation generators. Thus, in a medical facility, such as a hospital, a Talbot capturing device will be introduced to a capturing room containing a preinstalled general capturing device, such as a radiation generator. In a hospital having multiple capturing rooms, Talbot capturing devices will be newly introduced to some or all of the multiple capturing rooms containing preinstalled general capturing devices.

In a diagnostic medical image system for general capturing preinstalled in a medical facility, an operator or radiologist operates a console before an X-ray capturing operation so as to obtain capturing order information on the X-ray capturing operation through a hospital information system (HIS) or a radiology information system (RIS). Capturing order information may be registered after capturing. The capturing order information contains essential information consisting of information on the patient and the conditions of capturing. General capturing is performed in accordance with the capturing order information selected by the operator or radiologist and image signals (also referred to as image data) corresponding to one image captured by the FPD is sent to the console. Data on dark readings for offset correction is subsequently transmitted, if necessary. The console performs various corrections, including offset correction, gain correction, and defective pixel correction to the image signals corresponding to one image, and then performs various image processing procedures, such as gradation processing, appropriate for the captured site to generate a diagnostic medical image.

The resulting diagnostic medical image is displayed on a display unit in the console, and is confirmed and saved in connection with the capturing order information by the operator or radiologist. The saved diagnostic medical image is sent to, for example, a picture archiving and communication system (PACS) together with the capturing order information so that medical doctors can review the image for diagnosis. A console of a conventional diagnostic medical image system for general capturing is operated in connection with a single capturing order information, image signals corresponding to one image captured by the FPD in accordance with the capturing order information, and a diagnostic medical image, so as to establish their 1:1:1 relationship.

If a separate console for a Talbot capturing device, which is introduced to such a diagnostic medical image system for general capturing, is installed to a conventional diagnostic medical image system for general capturing provided with a preinstalled console, the operator or radiologist needs to operate two separate consoles, which leads to complicated operation of the entire system. For example, two separate consoles need to be used if a conventional general capturing system and a Talbot capturing device are installed in a single capturing room. To avoid this, a console preinstalled in a medical facility, e.g., hospital, of a diagnostic medical image system for general capturing may be operated to perform the above-described process in a conventional diagnostic medical image system for general capturing and the processing of moire images captured by the newly introduced Talbot capturing device.

A Talbot capturing device can generate several types of diagnostic medical images having different characteristics, e.g., absorption images, differential phase images, and small-angle scattering images, and a different number of moire images is required for the generation of such images (i.e., the numbers of capturing operations and radiation exposures), i.e., one moire image for Fourier transform and multiple moire images for a Talbot or Talbot-Lau interferometer. That is, one piece of capturing order information, image signals corresponding to one or more moire images captured by an X-ray detector in accordance with the capturing order information, and the several types of diagnostic medical images are linked to establish their 1:m:n relationship.

Under such circumstances, a preinstalled console of a diagnostic medical image system for general capturing links capturing order information to a diagnostic medical image to establish their 1:1 relationship, as described above; thus, only one image of the several types of diagnostic medical images reconstructed and generated from moire images, e.g., absorption images, differential phase images, and small-angle scattering images, is probably linked to the corresponding capturing order information. Thus, the other diagnostic medical images are probably discarded.

Such an incident can probably be prevented by modifying the processing of the console so that the several types of diagnostic medical images, e.g., absorption images, differential phase images, and small-angle scattering images, reconstructed and generated from one or more moire images captured by the Talbot capturing device is linked to the corresponding capturing order information. Unfortunately, if a console is configured this way, a conventional diagnostic medical image system for general capturing may obtain image signals corresponding to one image through one irradiation operation of an FPD with X-ray beams irradiated from an X-ray source and passing through a subject, and the console may generate one diagnostic medical image from the image signals and link the resulting diagnostic medical image to the corresponding capturing order information, but the console will probably determine other remaining diagnostic medical images yet to be linked to the capturing order information. Such an erroneous determination will cause the console to wait for the remaining diagnostic medical images even though the captured diagnostic medical image is correctly linked to the corresponding capturing order information. This prevents the establishment of the diagnostic medical image, and thus, the capturing process will not end.

Such a problem readily occurs as a result of introduction of a Talbot capturing device into an existing diagnostic medical image system for general capturing in a medical facility, e.g., hospital, as described above, but also may occur in any diagnostic medical image system including both a general-purpose capturing system and a Talbot capturing device. A diagnostic medical image system including both a general-purpose capturing system and a Talbot capturing device processes various types of data including data corresponding to one diagnostic medical image captured with a general-purpose capturing system, data on multiple moire images captured by the Talbot capturing device, and data on the several types of diagnostic medical images reconstructed and generated from the moire images. The data on diagnostic medical images (data on moire images generated with the X-ray detector) used for the generation (reconstruction) of multiple diagnostic medical images may correspond to one image or multiple images. Thus, data on one diagnostic medical image and data on multiple diagnostic medical images coincide in the system.

This will accelerate the problems described above and may cause confusion in the operation of the diagnostic medical image system. As described above, data on one diagnostic medical image captured by the general-purpose capturing system, image signals corresponding to one or more moire images, and data on the several types of diagnostic medical images captured by the Talbot capturing device coincide in the system. Thus, the data on the diagnostic medical image may be linked to unrelated capturing order information, or a diagnostic medical image captured by a general-purpose capturing unit may be erroneously linked to unrelated capturing order information that is linked to several types of diagnostic medical images.

An object of the present invention, which has been conceived to solve the problems described above, is to provide a diagnostic medical image system that includes both a general-purpose capturing unit and a Talbot capturing device (i.e., an X-ray capturing device including a Talbot or Talbot-Lau interferometer or involving Fourier transform) and can correctly link a diagnostic medical image generated by any of the above capturing units to corresponding capturing order information.

Means for Solving the Problem

To solve the problems described above, a diagnostic medical image system includes:
a first capturing unit including:
an X-ray source which irradiates X-ray beams; and
an X-ray capturing device which reads the X-ray beam irradiated from the X-ray source and passing through a subject as an image signal, the first capturing unit reading the image signal corresponding to one image generated at the X-ray capturing device through one irradiation operation of the X-ray capturing device with the X-ray beam irradiated from the X-ray source and passing through the subject;
a console which receives the image signal corresponding to one image from the first capturing unit, generates one diagnostic medical image from the received image signal corresponding to one image, and links the one generated diagnostic medical image to one corresponding capturing order information;
a second capturing unit including:
an X-ray source;
a plurality of gratings; and
an X-ray detector which includes a two-dimensional array of transducers generating electrical signals in response to the X-ray beams irradiated from the X-ray source and passing through the subject and the plurality of gratings and reads the electrical signals generated at the transducers as image signals, the second capturing unit reading the image signals corresponding to multiple images generated at the X-ray detector through multiple irradiation operations of the X-ray detector with the X-ray beams irradiated from the X-ray source and passing through the subject and the plurality of gratings; and
a controller which reconstructs and generates several types of diagnostic medical images from the image signals corresponding to multiple images read by the second capturing unit, wherein,
the controller consolidates the generated several types of diagnostic medical images and sends the consolidated diagnostic medical images to the console; and
the console links the consolidated several types of diagnostic medical images sent from the controller to one corresponding capturing order information, through a process identical to the process of linking the one diagnostic medical image captured by the first capturing unit to one capturing order information.

A method of introducing a Talbot capturing device to a diagnostic medical image system for general capturing including an X-ray source which irradiates X-ray beams, an FPD which reads electrical signals generated by a two-dimensional array of transducers, which generate electrical signals corresponding to X-ray beams irradiated from an X-ray source through a subject, as image signals, and a console which links one diagnostic medical image generated from the image signal corresponding to one image received from the X-ray capturing device to one corresponding capturing order information, the FPD reading the image signal corresponding to one image through one irradiation operation of the FPD with the X-ray beams irradiated from the X-ray source and passing through a subject, the method including:
introducing the Talbot capturing device including an X-ray source, a plurality of gratings, and an X-ray detector which includes a two-dimensional array of transducers generating electrical signals in response to the X-ray beams irradiated from the X-ray source and passing through the subject and the plurality of gratings and reads the electrical signals generated at the transducers as image signals, the X-ray detector reading the image signal corresponding to one image through one irradiation operation of the X-ray detector with the X-ray beams irradiated from the X-ray source and passing through the subject and the gratings; and
operating the console to reconstruct and generate several types of medical images from the image signal corresponding to one image, to consolidate the generated several types of medical images, and to link the generated several types of medical images to one corresponding capturing order information, upon reception of the image signal corresponding to one image from the Talbot capturing device.

A method of introducing a Talbot capturing device to a diagnostic medical image system for general capturing comprising an X-ray source which irradiates X-ray beams, an X-ray capturing device which reads the X-ray beams irradiated from the X-ray source and passing through a subject as image signals, and a console which links one diagnostic medical image generated from the image signal corresponding to one image received from the X-ray capturing device to one corresponding capturing order information, the X-ray capturing device reading the image signal corresponding to one image through one irradiation operation of the X-ray capturing device with the X-ray beams irradiated from the X-ray source and passing through a subject, the method comprising:

introducing the Talbot capturing device comprising an X-ray source, a plurality of gratings, and an X-ray detector which includes a two-dimensional array of transducers generating electrical signals in response to the X-ray beams irradiated from the X-ray source and passing through the subject and the plurality of gratings and reads the electrical signals generated at the transducers as image signals, the X-ray detector reading the image signal corresponding to one image through one irradiation operation of the X-ray detector with the X-ray beams irradiated from the X-ray source and passing through the subject and the gratings;

consolidating the generated several types of diagnostic medical images and sending the consolidated diagnostic medical images to the console with a controller which reconstructs and generates several types of diagnostic medical images from the image signal corresponding to one image received from the Talbot capturing device; and operating the console to link the consolidated several types of diagnostic medical images sent from the controller to one corresponding capturing order information.

Advantageous Effects of Invention

In the diagnostic medical image system according to the present invention, the controller consolidates several types of diagnostic medical images reconstructed from multiple moire images captured by the second capturing unit into a single data item or group, and sends the consolidated diagnostic medical images to the console, and the console collectively links the several types of diagnostic medical images, which are consolidated into a single data item or group, to a corresponding capturing order information to establish their 1:1 relationship, through a process identical to that of linking the diagnostic medical image captured through a general capturing operation to capturing order information (so as to establish their 1:1 relationship). Alternatively, the controller consolidates image signals corresponding to multiple moire images captured by the second capturing unit into a single data item or group and sends this to the console. The console then reconstructs and generates several types of diagnostic medical images from the image signals corresponding to the multiple moire images.

This links the several types of diagnostic medical images in the form of a single data item or group to capturing order information. Thus, all of the several types of diagnostic medical images reconstructed from the moire images captured through X-ray capturing performed by the second capturing unit in accordance with the capturing order information can be correctly linked to the capturing order information. This certainly prevents the linking of only one or few of the several types of the diagnostic medical images reconstructed from the moire images captured by the second capturing unit to the capturing order information, which also causes the non-linking of the remaining diagnostic medical images to the capturing order information, or the erroneous determination by the console that other diagnostic medical images remain to be linked to the capturing order information in addition to the diagnostic medical image captured by the first capturing unit, so as to prevent the capturing process from not ending.

Data on one diagnostic medical image captured by the first capturing unit, data on multiple moire images captured by the Talbot capturing device, and data on the several types of diagnostic medical images reconstructed and generated from the moire images coincide in the system. Thus, the data on the diagnostic medical image can be prevented from being erroneously linked to unrelated capturing order information, or a diagnostic medical image captured by a general-purpose capturing unit can be certainly prevented from being erroneously linked to unrelated capturing order information that is already linked to several types of diagnostic medical images.

BRIEF DESCRIPTION OF DRAWINGS

FIG. 3 is a block diagram illustrating an equivalent circuit of an FPD.

FIG. 4 illustrates example capturing order information.

FIG. 5 illustrates an example selection menu displaying capturing order information.

EMBODIMENT FOR CARRYING OUT THE INVENTION

Embodiments of a diagnostic medical image system according to the present invention will now be described with reference to the accompanying drawings.

In the description below, a first capturing unit includes an X-ray source and an X-ray capturing device for general capturing, and reads image signals corresponding to one image captured with an X-ray capturing device irradiated once with X-ray beams irradiated from an X-ray source and passing through a subject; and a second capturing unit includes a Talbot capturing device (i.e., an X-ray capturing device including a Talbot or Talbot-Lau interferometer, or involving Fourier transform) and reads image signals corresponding to multiple images with an X-ray detector irradiated multiple times with X-ray beams irradiated from an X-ray source through a subject and multiple gratings. In brief, the diagnostic medical image system according to this embodiment includes both the first and second capturing units.

First Embodiment

Figure 1:
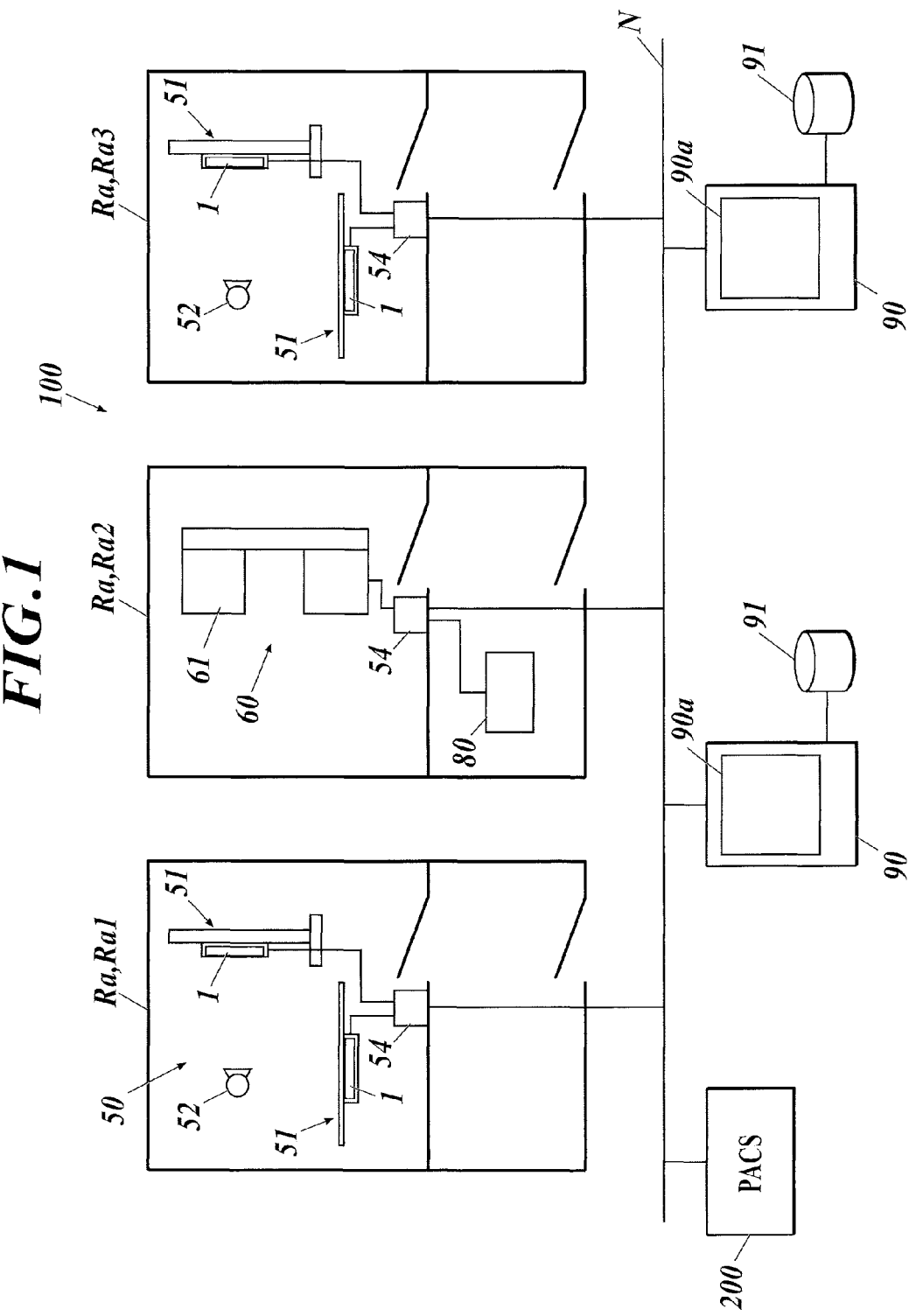
FIG. 1 illustrates an example configuration of a diagnostic medical image system according to an embodiment.

FIG. 1 illustrates an example configuration of a diagnostic medical image system according to a first embodiment of the present invention. In this embodiment, a diagnostic medical image system 100 includes a plurality of capturing rooms Ra (Ra1 to Ra3) and a plurality of consoles 90. Components in the capturing rooms Ra are connected to the consoles 90 via a network N. In this embodiment, the diagnostic medical image system 100 is connected to a PACS 200 via the network N, and also to HISs and RISs via the network N, although not shown in the drawings.

In the diagnostic medical image system 100 illustrated in FIG. 1, capturing rooms Ra containing first capturing units 50 (i.e., capturing rooms Ra1 and Ra3) do not contain second capturing units 60, whereas a capturing room Ra containing a second capturing unit 60 (i.e., capturing room Ra2) does not contain a first capturing unit 50. Alternatively, a single capturing room Ra may contain both a first capturing unit 50 and a second capturing unit 60. For example, a single capturing room Ra may contain a first capturing unit 50, a second capturing unit 60, and a console 90. The first capturing unit 50 and the second capturing unit 60 are both to be provided in the diagnostic medical image system 100 according to this embodiment, and the configuration is not limited to the system illustrated in FIG. 1.

[First Capturing Unit]

Figure 2:
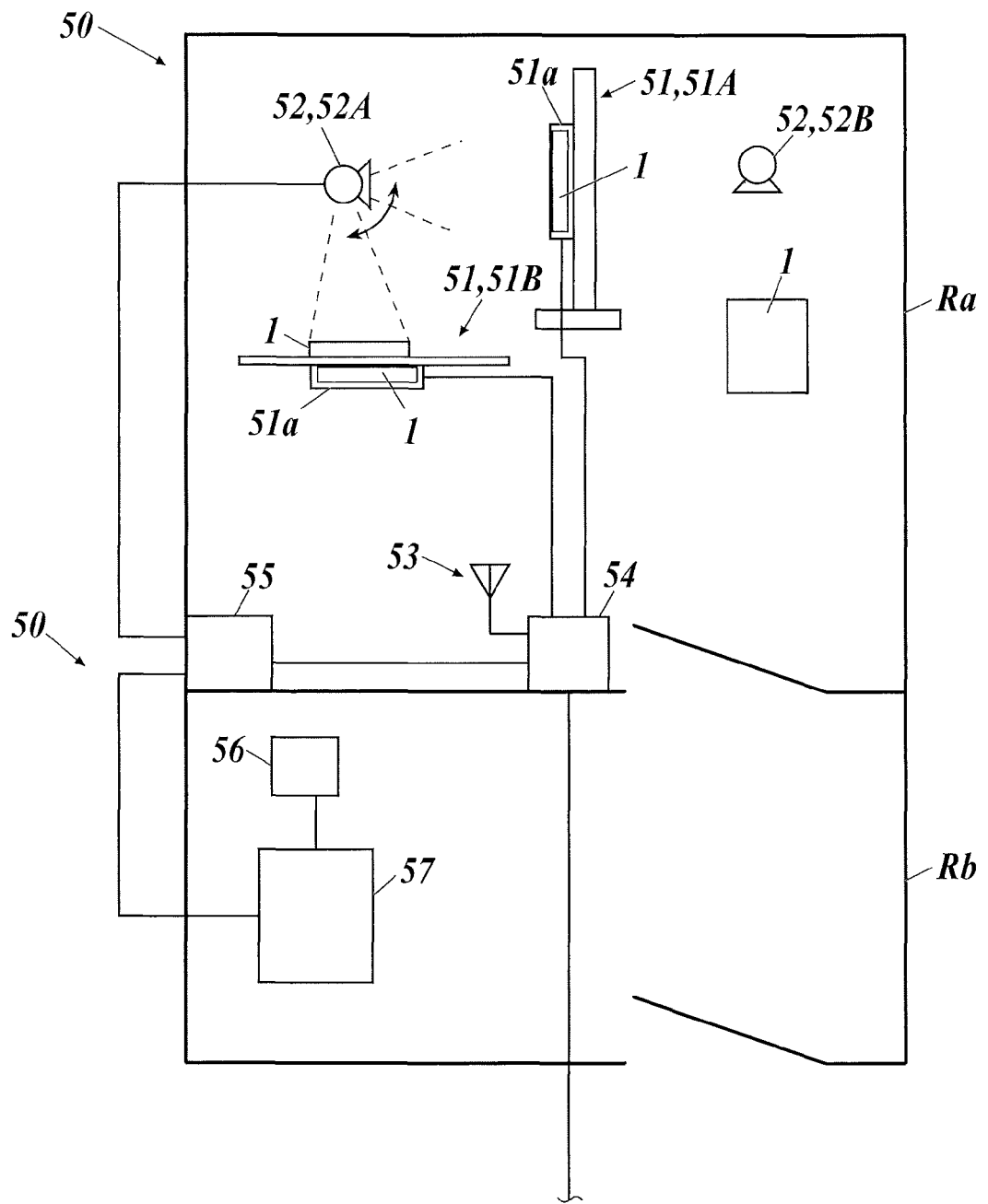
FIG. 2 illustrates a specific example configuration of a first capturing unit.

The configuration of a first capturing unit 50 will now be described. With reference to FIG. 2, the first capturing unit 50 includes an X-ray source 52 and an FPD 1. Details will now be described. A first capturing unit 50 including an FPD 1 serving as an X-ray capturing device will now be described. Alternatively, the X-ray capturing device in the first capturing unit 50 may be the CR unit described above (i.e., a CR cassette containing a photostimulable phosphor sheet, which is mentioned above, or a composite device of a photostimulable phosphor sheet and an image reader). The X-ray capturing device of the first capturing unit 50 according to the present invention should not be limited to an FPD 1. It is well known that image signals in a CR cassette serving as an X-ray capturing device of the first capturing unit 50 are read from the CR cassette by an image reader (not shown) and sent from the image reader to a console 90, which is described below (see FIG. 1). In the following description, the FPD 1 used in the first capturing unit 50 is a portable (or cassette) FPD. Alternatively, a stand-alone (fixed-mount) FPD integrated with a base may be used, for example.

[FPD]

The FPD 1 in the first capturing unit 50 will now be described. FIG. 3 is a block diagram illustrating an equivalent circuit of the FPD 1 according to this embodiment. With reference to FIG. 3, the FPD 1 includes a two-dimensional array (or a matrix) of transducers 7 on a sensor substrate (not shown). The transducers 7 generate electrical signals corresponding to X-ray beams irradiated from an X-ray source 52, which is described below (see FIG. 2), and passing through a subject (not shown). The transducers 7 are connected to bias lines 9. The bias lines 9 are bundled into a connecting line 10, which is connected to a bias supply 14. The bias supply 14 applies an inverse bias voltage to the transducers 7 via the bias lines 9. The transducers 7 are connected to thin film transistors (TFTs) 8, which serve as switching devices and are connected to signal lines 6.

In a scan driver 15, a power circuit 15a supplies ON and OFF voltages to a gate driver 15b via a line 15c. The gate driver 15b switches the ON and OFF voltages applied to lines L1 to Lx of scanning lines 5. The TFTs 8 are turned on in response to an ON voltage applied via the scanning lines 5 to electrically connect the transducers 7 and the signal lines 6 and read the electrical signals from the transducers 7. The TFTs 8 are turned off in response to an OFF voltage applied via the scanning lines 5 to electrically disconnect the transducers 7 and the signal lines 6.

A controller 22 includes a central processing unit (CPU), a read only memory (ROM), a random access memory (RAM), a computer including an input/output interface connected to a bus, and a field programmable gate array (FPGA) (which are all not shown). The controller 22 may be composed of a dedicated control circuit. The controller 22 is connected to a storage unit 23 including a static RAM (SRAM) or synchronous DRAM (SDRAM), and an antenna unit 41 for communication with external units. The controller 22 is also connected to a battery 24 that supplies electrical power required for functional units, e.g., a scan driver 15, a reader circuit 17, a storage unit 23, and a bias supply 14.

The controller 22 reads an image signal D after X-ray beams are irradiated from the X-ray source 52 (described below) and passing through a subject (not shown) through sequential application of an ON voltage to each scanning line 5 from the gate driver 15b, so as to sequentially turn on the TFTs 8 on the scanning line 5. The TFTs 8 in an ON state electrically connects the transducers 7 with the respective signal lines 6. The electrical signals from the transducers are read by the respective reader circuits 17 in a reader IC 16. Specifically, amplifier circuits 17 output voltage values depending on the charges applied from the transducers 7 to the corresponding amplifier circuits 18 in the reader circuits 17.

Each correlated double sampling circuit ("CDS" in FIG. 3) 19 outputs to the downstream side an analog image signal D corresponding to the difference between the voltage values output from the corresponding amplifier circuits 18 before and after charges are applied from the corresponding transducer 7. The output image signals D are sequentially sent to an A/D converter 20 via an analog multiplexer 21, sequentially converted to digital image signals D at the A/D converter 20, and sequentially output and stored in the storage unit 23. The reading process of electrical signals D from the transducers 7 is carried out as described above. After capturing, the image signals D stored in the storage unit 23 can be sent to an external console 90 (see FIG. 1) via the antenna unit 41.

[Other Components in First Capturing Unit]

Other components in the first capturing unit 50 will now be described. In this embodiment, bucky devices 51 are installed in the capturing rooms Ra. Each bucky device 51 has a cassette holder 51a that can hold the FPD 1. With reference to FIGS. 1 and 2, a standing position capturing bucky device 51A and a lying position capturing bucky device 51B are both installed as the bucky device 51. Alternatively, both bucky devices do not always need to be installed, and either one of the bucky devices may be installed.

With reference to FIG. 2, the first capturing unit 50 includes at least one X-ray source 52A that irradiates X-ray beams onto the FPD 1 loaded in a bucky device 51 through a subject (not shown). The FPD 1 can be used independently without the bucky device 51; the FPD 1 can be disposed against the body of a patient (not shown) lying on the lying position capturing bucky device 51b or a bed carried into the capturing room Ra. In such a case, a portable X-ray source 52B may be used in place of the X-ray source 52.

Each capturing room Ra is covered with lead plates (not shown) to prevent X-rays from leaking outside from the capturing room Ra. The lead plates prevent communication from and to the capturing room Ra. Thus, the capturing room Ra is provided with a relay (also referred to as base station) 54 for relaying the communication between units inside the capturing room Ra and units outside the capturing room Ra. In this embodiment, the relay 54 includes an access point 53 so that the FPD 1 can wirelessly transmit and receive signals such as image signals D. The relay 54 is connected to a radiation generator 55 and a console 90. The relay 54 includes a converter (not shown) that converts signals for LAN (local area network) communication to be sent from the FPD 1 or console 90 to the radiation generator 55 into signals for the radiation generator 55, or vice versa.

An operating table 57 of the radiation generator 55 is installed in a front chamber (operating chamber) Rb according to this embodiment. The operating table 57 includes an exposure switch 56 to be operated by an operator or radiologist to instruct the irradiation of X-ray beams from the X-ray source 52. The radiation generator 55 carries out various control operations, for example, adjustment of the X-ray source 52 for an appropriate dose of X-ray beams.

In the first capturing unit 50 having the configuration described above, the FPD 1 loaded in the bucky device 51 or a FPD 1 used alone not loaded to the bucky device 51 is irradiated once with X-ray beams irradiated from the X-ray source 52 (see FIG. 2) and passing through a subject (not shown) and reads image signals D corresponding to one diagnostic medical image. That is, the diagnostic medical image system 100 according to this embodiment performs general capturing with the FPD 1 in the first capturing unit 50.

[Console]

Before description on the second capturing unit 60, the configuration of the consoles 90 will now be described. An example configuration of a console 90 for performing general capturing with the first capturing unit 50 will now be described. In this embodiment, the console 90 consists of a computer. Alternatively, the console 90 may consist of a dedicated unit. With reference to FIG. 1, the console 90 includes a display 90a consisting of a cathode ray tube (CRT) or a liquid crystal display (LCD) and input units such as a mouse and a keyboard (not shown). The console 90 is connected to an internal or external storage unit 91 such as a hard disk drive (HDD).

In this embodiment, the HIS or RIS described above (not shown in the drawing) is connected to the network N illustrated in FIG. 1 so that the console 90 can receive registered capturing order information from the HIS or RIS. As described above, capturing order information can be registered through input on the console 90 after X-ray capturing. Any input means may be used for inputting capturing order information to the console 90, for example, reading a barcode on a sheet with a barcode reader (not shown).

With reference to the example illustrated in FIG. 4, capturing order information contains assigned parameters associated with patient information consisting of "patient ID" P2, "patient name" P3, "sex" P4, "age" P5, and "clinical department name" P6, and capturing conditions consisting of "captured site" P7, "capturing direction" P8, and "bucky device ID" P9 of the bucky device to be used. With reference to the example illustrated in FIG. 4, the parameters "001" and "002" for the bucky device ID indicate standing position capturing and lying position capturing bucky device 51A and 51B, respectively, and the parameter "003" for the bucky device ID indicates a FPD 1 used alone not loaded to a bucky device 51. "Capturing order IDs" P1 are automatically assigned to the capturing order information in the order of registration. The console 90 receives the capturing order information and displays a list of the capturing order information on a selection menu H1 on the display 90a of the console 90 as illustrated in FIG. 5.

In this embodiment, the selection menu H1 includes a capturing order information display column h11 that displays the list of capturing order information and selection buttons h12 for selection of the capturing order information corresponding to a capturing operation to be performed. An enter button h13 and a return button h14 are disposed below the capturing order information display column h11. For example, an operator or radiologist clicks the selection buttons h12 corresponding to a scheduled X-ray capturing operation to select all of the four pieces of capturing order information displayed for patient "M," and clicks the enter button h13 to instruct the console 90 to display a screen H2, such as that illustrated in FIG. 6, on the display 90a.

In this embodiment, icons I1 to I4 corresponding to the selected capturing order information are displayed in the order of the capturing order information IDs for the selected capturing order information, i.e., in the order of the left top, right top, left bottom, and then right bottom in the central area of the screen H2. The icons I can be rearranged. The icons I1 to I4 contain representations of the bucky devices 51 assigned by the corresponding capturing order information (see icons I1 to I3) and a FPD (see icon I4) used alone if a bucky device 51 is not assigned (i.e., if the parameter for the bucky device ID is "003"), and further contain parameters for the tube current, the captured site, and the direction of capturing. A display Ia for assigning the irradiation conditions is displayed in the right area of the screen H2. The operator or radiologist can click on the "+" and "−" buttons of the items in the menu Ia to vary the irradiation conditions.

Figure 6:
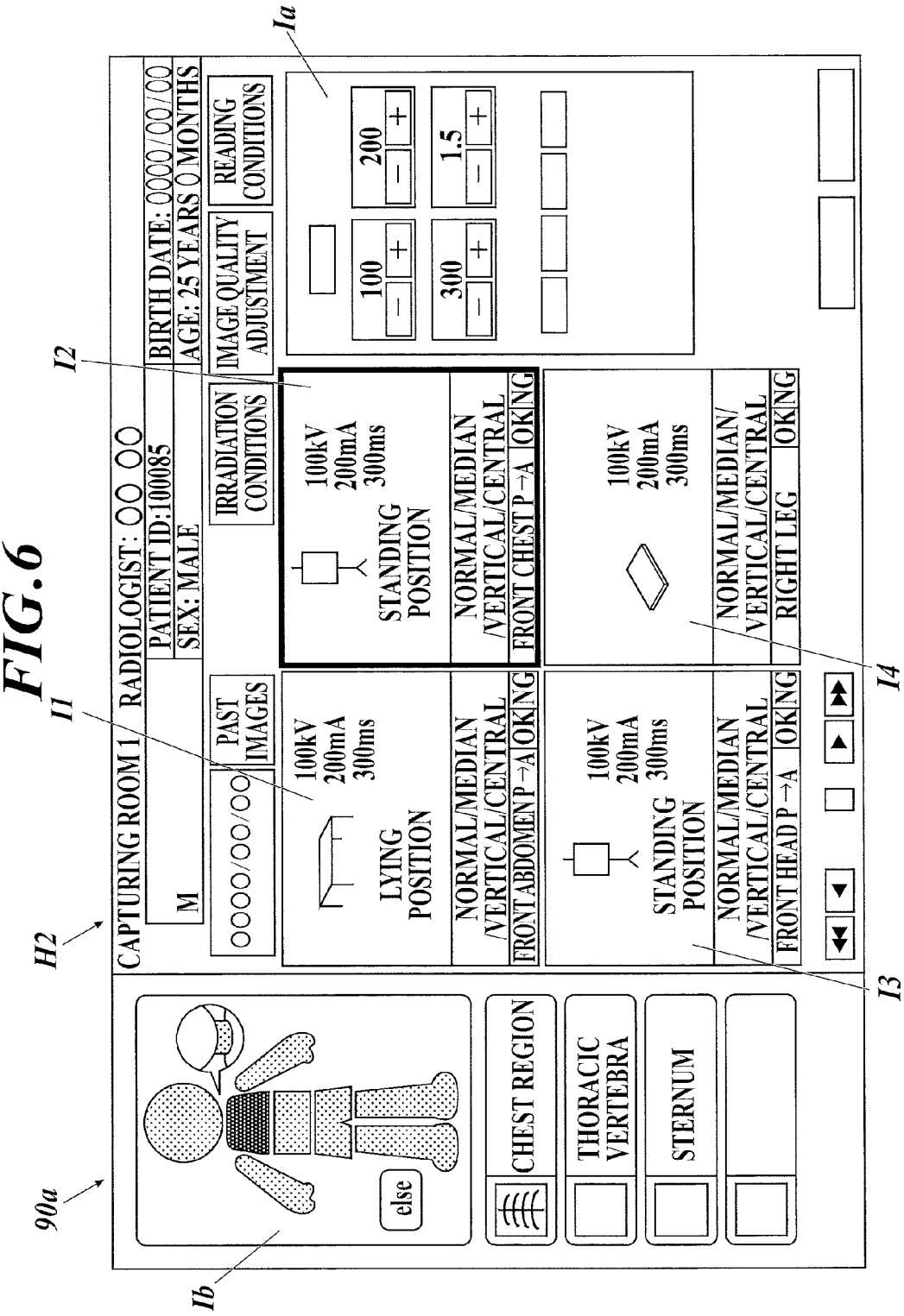
FIG. 6 illustrates an example menu displaying icons corresponding to the selected capturing order information.

The icon I corresponding to the next X-ray capturing operation (icon 12 in FIG. 6) is emphasized in the screen H2. In this embodiment, the irradiation conditions, such as the tube current, displayed in the emphasized icon I (or the changed irradiation conditions if the irradiation conditions are changed through the menu Ia) are sent to the radiation generator 55 (see FIG. 1), and the irradiation conditions such as the tube current are automatically established in the radiation generator 55. A human body model Ib, which is readily visible by the operator, is displayed in the left area of the screen H2 that indicates the site to be captured assigned in the capturing order information corresponding to the emphasized icon I. With reference to FIG. 6, the icon 12 assigning the capturing of the front chest is emphasized, and thus the chest section of the human body model Ib is displayed differently (for example, colored red) compared to the other sections.

For example, X-ray capturing is performed in the capturing room Ra1 (see FIG. 1) based on the capturing order information corresponding to the emphasized icon I on the console 90; in response, the controller 22 of the FPD 1 reads the image signals D from the transducers 7 and sends the image signals D to the console 90 via the antenna unit 41 (see FIG. 3), the bucky device 51 (see FIG. 1), and the relay 54, as described above.

Figure 7:
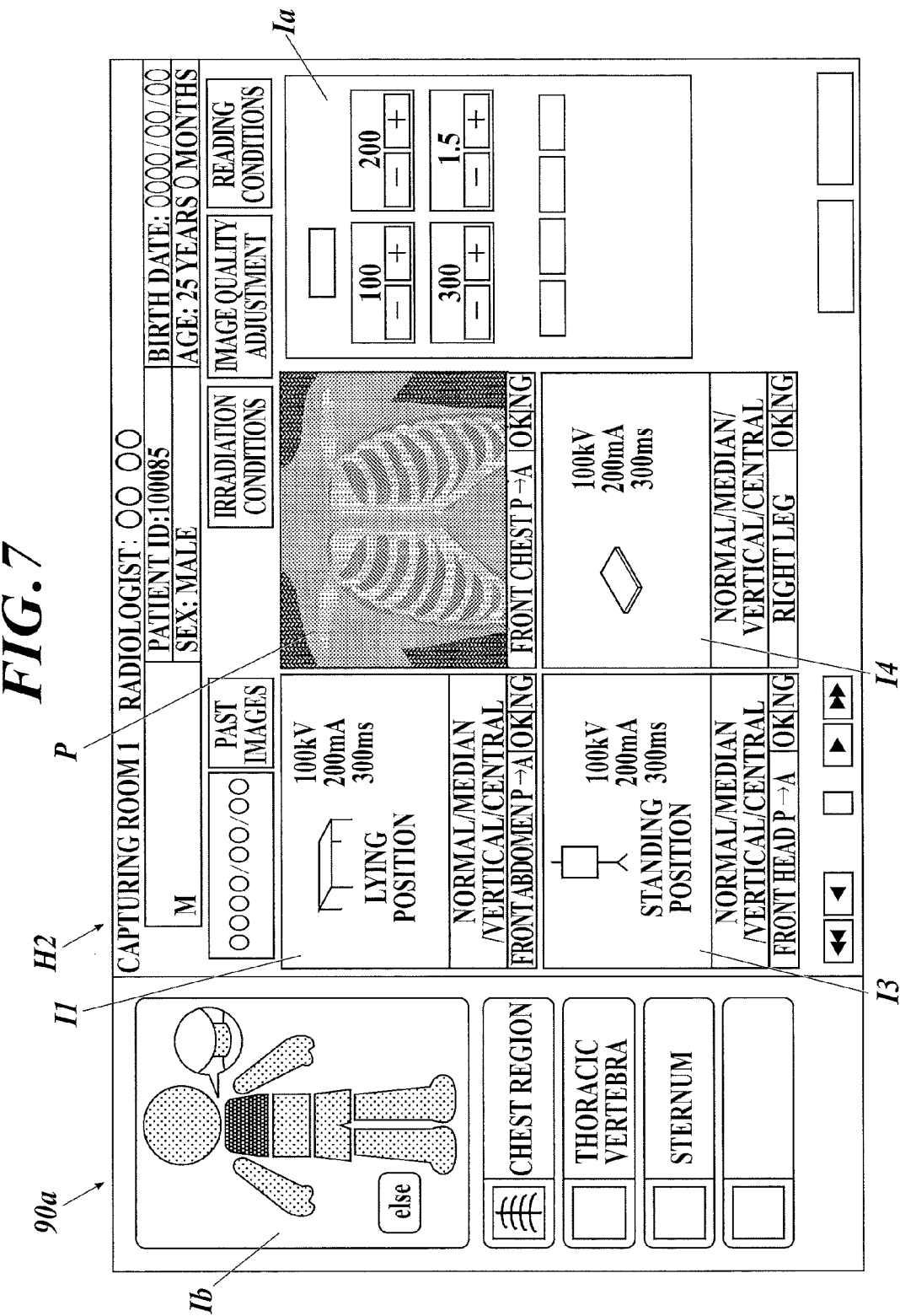
FIG. 7 illustrates a displayed diagnostic medical image generated at the position where a selected icon was originally displayed.

The console 90 receives the image signals D from the FPD 1, and carries out precise image processing on the image signals D, including offset correction, gain correction, defective pixel correction, and gradation processing, appropriate for the captured site, so as to generate a diagnostic medical image (normally an absorption image). The console 90 generates the diagnostic medical image, and in the case exemplified in FIG. 6, displays the resulting diagnostic medical image p in the icon 12 in the screen H2 displayed on the display 90a of the console 90, as illustrated in FIG. 7, for example. The console 90 confirms and saves the resulting diagnostic medical image p in connection with the capturing order information corresponding to the icon 12 (i.e., the capturing order information associated with the X-ray capturing of the diagnostic medical image), unless the operator or radiologist, observing the displayed diagnostic medical image p clicks the ON button or the NG button within a determined time. As described above, the diagnostic medical image p saved in connection with the capturing order information is sent together with the capturing order information from the console 90 to a PACS connected to the network N (see FIG. 1) for diagnostic review by a medical doctor.

As described above, the first capturing unit 50 performs general capturing involving one irradiation operation of the FPD 1 with X-ray beams from the X-ray source 52 (see FIG. 2) and passing through a subject to read the image signals D corresponding to one diagnostic medical image at the FPD 1. Thus, in general capturing performed at the first capturing unit 50, the console 90 saves the diagnostic medical image p in connection with the corresponding capturing order information, as described above.

As described above, if the X-ray capturing device in the first capturing unit 50 consists of a CR device, the console 90 generates a diagnostic medical image p based on the image signals D sent from the image reader reading the image signals from the CR cassette, and saves the resulting diagnostic medical image in connection with the corresponding capturing order information associated with the X-ray capturing operation performed for the diagnostic medical image after approval of the diagnostic medical image by the operator or radiologist. In such general capturing with the CR device in the first capturing unit 50, the CR device is irradiated once with X-ray beams irradiated from the X-ray source 52 (see FIG. 2) and passing through a subject and reads the image signals D corresponding to one diagnostic medical image. Thus, also in general capturing by the CR device in the first capturing unit 50, the console 90 links the diagnostic medical image p saved as described above to the corresponding capturing order information.

[Second Capturing Unit]

Figure 8:
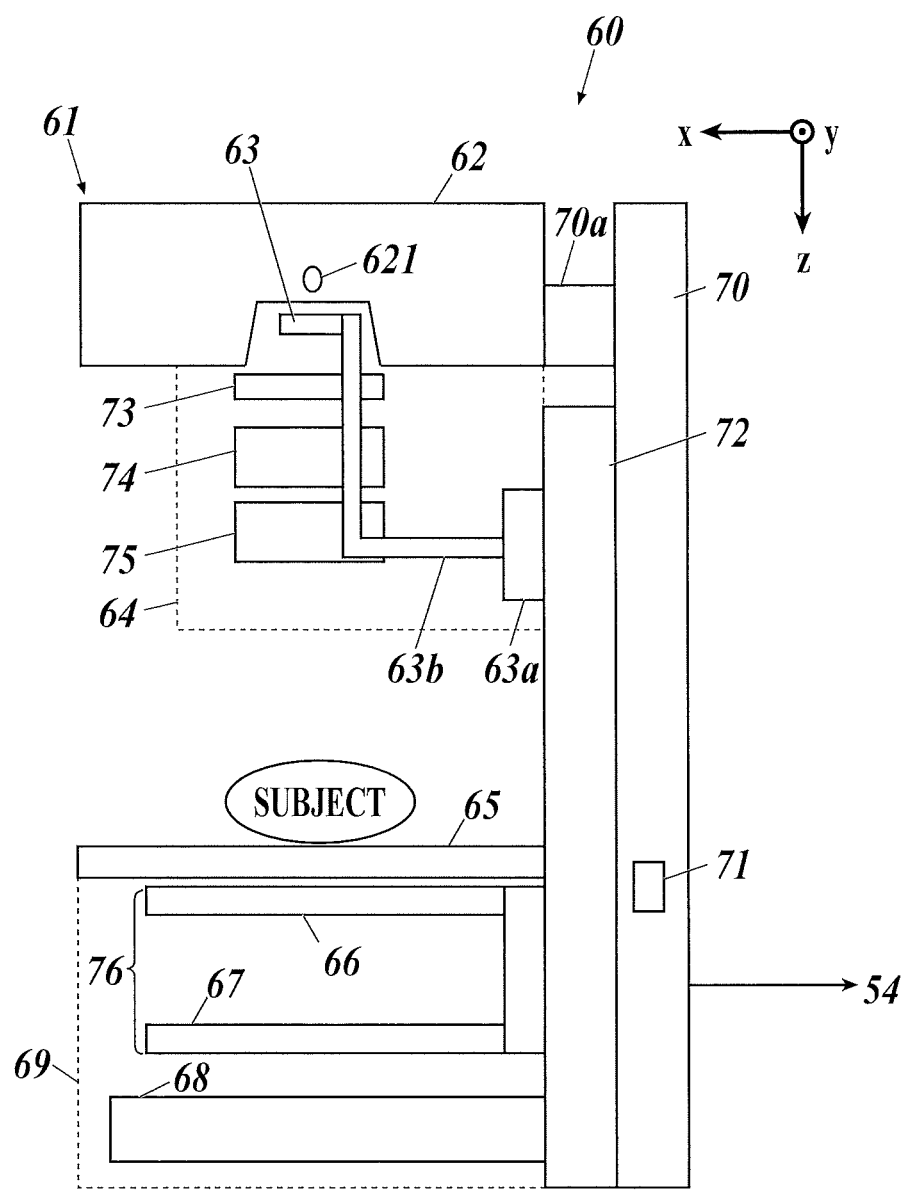
FIG. 8 illustrates an example configuration of a Talbot capturing device in a second capturing unit.

The configuration of a second capturing unit 60 will now be described. In this embodiment, the second capturing unit 60 consists of a Talbot capturing device including an X-ray source 62, a plurality of gratings 63, 66, and 67, and an X-ray detector 68, as illustrated in FIG. 8, for example. Alternatively, the second capturing unit 60 according to this embodiment may consist of a Talbot capturing device including the Talbot interferometer described in patent literature 4, for example. A Talbot capturing device 61 including a Talbot-Lau interferometer, which is the Talbot capturing device in the second capturing unit, will now be described. As described above, the Talbot capturing device in the second capturing unit may be a Talbot capturing device including a Talbot interferometer or an X-ray capturing device involving Fourier transform.

Details will now be described. FIG. 8 schematically illustrates the second capturing unit. With reference to FIG. 8, the Talbot capturing device 61 of the second capturing unit 60 includes an X-ray source 62, a first cover unit 64 having a multislit grating 63, a second cover unit 69 including a subject table 65, a first grating 66, a second grating 67, and an X-ray detector 68, a supporting column 70, a body 71, and a base 72. The Talbot capturing device 61 illustrated in FIG. 8 is a vertical type including the X-ray source 62 (where reference numeral 621 denotes the focus of the X-ray source), the multislit grating 63, the subject table 65, the first grating 66, the second grating 67, and the X-ray detector 68 are arrayed in sequence along the gravity direction or z direction. The z direction is the direction of the irradiation axis of the X-ray beams irradiating from the X-ray source 62. With reference to FIG. 8, the components in the first cover unit 64 denoted by reference sign 63a is an adjuster, reference sign 63b is an attachment arm, reference sign 73 is an additional filter, reference sign 74 is an irradiation field diaphragm, and reference sign 75 is an irradiation field lamp. The components in the second cover unit 69 denoted by reference sign 76 is a grating unit including the first grating 66 and the second grating 67.

In this embodiment, the components in the first and second cover units 64 and 69 are covered with protective covers (not shown). If the Talbot capturing device 61 captures moire images through fringe scanning, the second cover unit 69 includes a mechanism (not shown) for moving the second grating 67 in a predetermined direction (the x direction in FIGS. 8 and 9), for example. The adjuster 63a finely adjusts the position of the multislit grating 63 in the x, y, and z direction and the rotational angle of the multislit grating 63 around the x, y, and z axes. The adjuster 63a may be optional if the multislit grating 63 can be fixed to the base 72 at high precision without the adjuster 63a. In FIG. 8, the reference sign 70a denotes a buffer to connect the X-ray source 62 and the supporting column 70.

Figure 9:
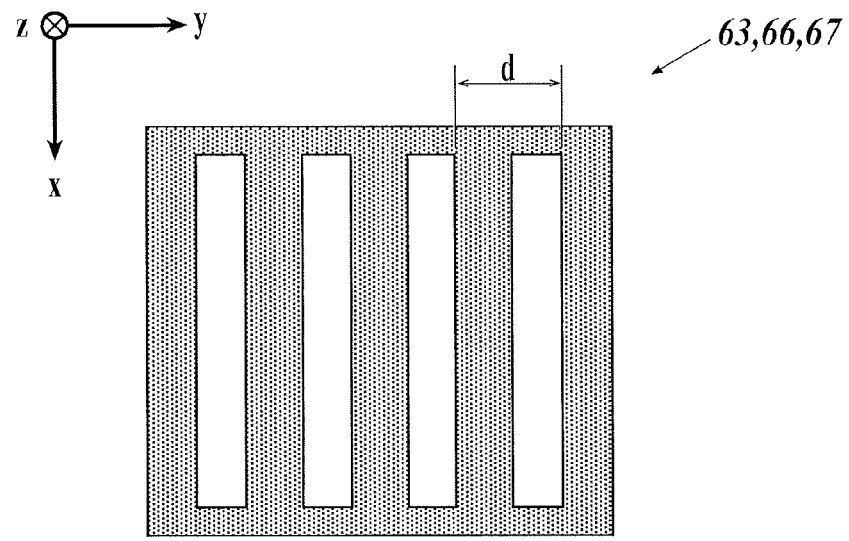
FIG. 9 is a schematic plan view of multislit grating, a first grating, and a second grating.

With reference to FIG. 9, the multislit grating 63 (also referred to as a G0 grating), the first grating 66 (also referred to as a G1 grating), and the second grating 67 (also referred to as a G2 grating) are grating which have multiple slits that are aligned along the x direction orthogonal to the X-ray irradiation direction or z direction. The materials and methods of production of these components are disclosed in Patent Literature 3. In FIG. 9, reference character d indicates the slit pitch of the multislit grating 63, the first grating 66, and the second grating 67.

[Principle of Talbot Capturing Device]

Figure 10:
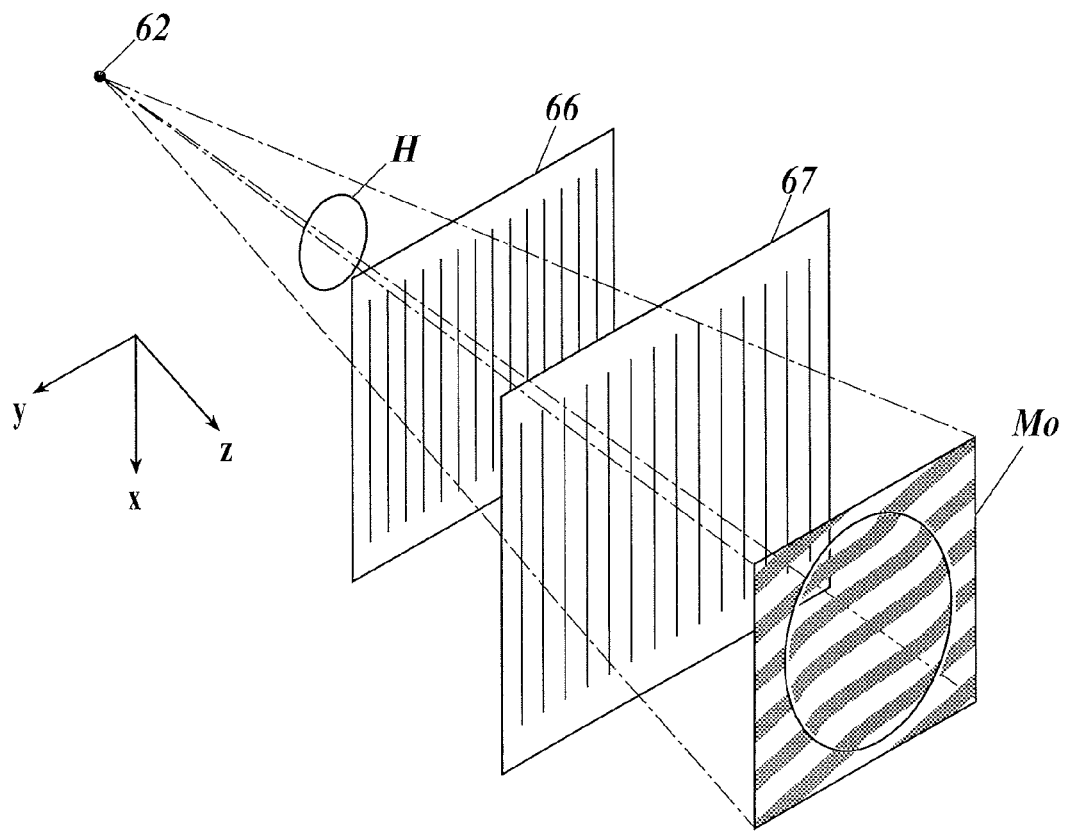
FIG. 10 illustrates the principle of a Talbot interferometer.

The principle common to all Talbot capturing devices 61 (including an X-ray capturing device involving Fourier transform) will now be described. With reference to FIG. 10, the X-ray beams irradiated from the X-ray source 62 pass through the first grating 66 and the X-ray beams which pass through form grating images along the z direction at a predetermined pitch. Such a grating image is referred to as a self-image. The phenomenon of forming such self-images along the z direction at a predetermined pitch is known as a Talbot effect.

The second grating 67 is disposed at a position of a self-image of the first grating 66 such that the grating direction of the second grating 67 (i.e., the extending direction of the slits (see the direction of the y axis in FIG. 9)) is disposed at a slight angle to the grating direction of the first grating 66, so as to form a moire image (denoted by reference characters Mo in FIG. 10) on the second grating 67. If the moire image Mo is illustrated on the second grating 67, it becomes difficult to understand. Therefore, the moire image Mo in FIG. 10 is illustrated at a position separated from the second grating 67. The moire image Mo is actually formed on and downstream of the second grating 67. FIG. 10 illustrates the effect of a subject H disposed between the X-ray source 62 and the first grating 66 on the moire image Mo, which is described below. If the subject H is not present, the moire image Mo contains only moire stripes.

The subject H disposed between the X-ray source 62 and the first grating 66 shifts the phase of the X-ray beams and cause distortion in the moire stripes of the moire image Mo at the boundary of the subject, as illustrated in FIG. 10. The moire image Mo is processed to detect the distortion in the moire stripes and reconstruct an image of the subject. This is the principle of a Talbot interferometer. Moire images Mo of coherent X-ray beams are captured before and after a subject H is disposed in front of the first grating 66, and are analyzed to reconstruct images of the subject, i.e., absorption image, differential phase image, and small-angle scattering image.

Figure 11:
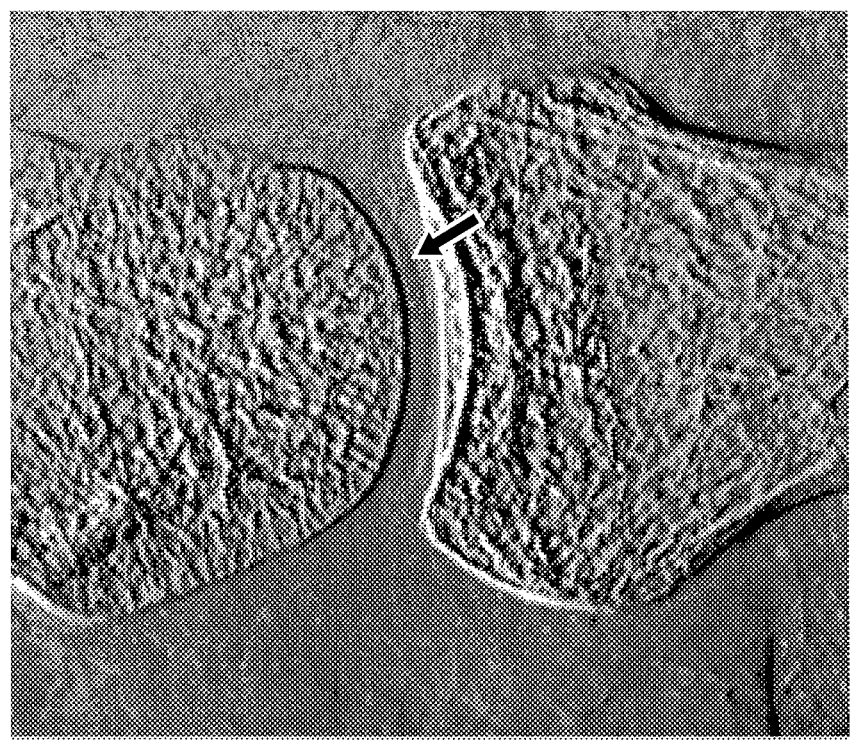
FIG. 11 illustrates an image of an edge of a cartilage portion of a joint portion captured in a differential phase image of the joint region.

The research conducted by the inventors has shown that a differential phase image reconstructed from the moire image Mo through capturing of a joint region in a non-dissected patient using the X-ray capturing device 61 may show the end of the cartilage portion between two bones in the joint as a streak indicated by the arrow in FIG. 11. Thus, the X-ray capturing device 61 can be used in place of a large capturing device involving MRI, for example, for at least capturing of a cartilage portion in a joint region of a patient.

[Other Components of Talbot Capturing Device]

Other components of the Talbot capturing device 61 illustrated in FIG. 8 include a subject table 65 for supporting the subject. The X-ray detector 68 has a configuration basically identical to that of the FPD 1 of the first capturing unit 50 (see FIG. 3). Although not illustrated in the drawing, the X-ray detector 68 includes a two-dimensional array of transducers that generate electrical signals in response to the X-ray beams irradiated from the X-ray source 62 and passing through the subject H and the gratings 63, 66, and 67, and reads the electrical signals generated at the transducers as image signals. The X-ray detector 68 may be a capturing unit, such as a charge coupled device (CCD) or an X-ray camera. As described above, the X-ray detector 68 has a structure substantially identical to that of the FPD 1 of the first capturing unit 50. Thus, the X-ray detector 68 may be provided in the form of a portable detector (i.e., cassette detector) that can also be installed in the first capturing unit 50. This form is preferred because a single X-ray detector 68 can be used as both an X-ray detector 68 and an FPD 1.

An increase in the distance between the X-ray detector 68 and the second grating 67 causes defocusing of the moire image Mo captured by the X-ray detector 68. Thus, usually, the X-ray detector 68 is fixed to the base 72 and is in contact with the second grating 67. The body 71 is connected to the X-ray source 62 and the X-ray detector 68 and controls the X-ray irradiation from the X-ray source 62. The body 71 also sends the image signals D corresponding to the moire image Mo read by the X-ray detector 68 to an external device, or generates a moire image Mo from the electrical signals D read by the X-ray detector 68 and sends information on the resulting moire image Mo to an external device.

The body 71 also comprehensively controls the Talbot capturing device 61 and includes appropriate units, such as an input unit, a display unit, and a storage unit (not shown). The capturing room Ra containing the Talbot capturing device 61 (capturing room Ra2 in the example illustrated in FIG. 1) is covered with lead plates (not shown) to prevent the X-ray beams from leaking outside. Thus, the Talbot capturing device 61 is also connected to external units, such as the console 90, via the relay 54, as illustrated in FIG. 1.

[Transducers in X-Ray Detector]

The transducers in the X-ray detector 68 may be any capturing device, for example, photodiodes, phototransistors, CCDs, or X-ray cameras. Alternatively, a CMOS (complementary metal oxide semiconductor) panel may be used. A CMOS panel can reduce the capturing time for one capturing operation compared to that of a panel including photodiodes. Thus, the time for capturing multiple moire images through fringe scanning can be reduced, for example, so as to reduce the burden on a patient. Unlike photodiodes, CMOS panels are advantageous in that residual images are not formed and thus residual image processing is unnecessary.

Unfortunately, CMOS panels have a drawback of a small saturation dose (i.e. upper limit of accumulated dose). That is, the dose required for capturing with the Talbot capturing device 61 causes relatively early saturation dose. A solution to such a problem of an X-ray detector 68 including a CMOS panel is to read the radiation multiple times (n times) during each radiation exposure to capture multiple (i.e., n) sub-moire images, unlike a conventional X-ray detector 68 including photodiodes that reads the radiation once for each radiation exposure to capture one moire image, for example. The values of the pixels in the n sub-moire images captured during a single radiation exposure can be added to combine and generate a single moire image. In such a case, it should be noted that the reading carried out during a single radiation exposure is to be completed before the transducers in the CMOS panel reach a saturation point.

In fringe scanning for capturing N moire images through N times of irradiation operations, the X-ray detector 68 having the configuration described above carries out the reading process n times for each radiation exposure, i.e., carries out the reading process N×n times to capture N×n sub-moire images. The n sub-moire images read during the same exposure period are combined to generate a single moire image, thereby generating N moire images in total.

The CMOS panel is readily affected by temperature. Thus, capturing is preferably carried out after stabilization of the overall temperature of the Talbot capturing device 61 including the X-ray detector 68 including the CMOS panel.

Thus, for example, the Talbot capturing device 61 including the X-ray detector 68 is preferably turned on in the morning of the day on which capturing is to be performed, so that the overall temperature of the Talbot capturing device 61 is stabilized by the time of the actual capturing.

[Method of Generating Several Types of Diagnostic Medical Images]

A method of reconstructing and generating several types of diagnostic medical images, i.e., absorption image, differential phase image, and small-angle scattering image, from the moire images Mo captured by the Talbot capturing device 61 will now be briefly described.

In this embodiment, the Talbot capturing device 61 performs fringe scanning to capture multiple moire images Mo by irradiating a subject with X-ray beams irradiated from the X-ray source 62 while the subject is supported on the subject table 65 and the second grating 67 is moved in a predetermined direction (the direction x in FIGS. 8 and 9). The several types of diagnostic medical images are reconstructed from the image signals corresponding to the multiple moire images Mo.

A background image is captured under the same conditions as those for images containing the subject. That is, a moire image Mo is captured by the X-ray detector 68 through irradiation of the X-ray beams without the subject disposed on the subject table 65. A background image may be captured before or after capturing of an image of the subject. However, background capturing for each capturing may readily damage the anode (not shown) of the X-ray source 62. Thus, alternatively, a background image may be captured immediately after starting up the Talbot capturing device 61 on the day capturing with the second capturing unit 60 is to be performed, for example. The resulting background moire image not containing the subject can be reused for every capturing operation performed on that day. A background moire image not containing a subject is hereinafter referred to as a BG moire image Mb, in distinction from a moire image Mo containing a subject. As described above, the signals obtained from the BG moire image Mb are referred to as background (BG) signals.

Artifacts caused by moire stripes might remain at an intolerable level in the images, e.g., absorption image, reconstructed from the BG moire image Mb captured immediately after start-up of the Talbot capturing device 61, for example. This suggests that the first grating 66 and the second grating 67 are distorted due to a variation in temperature that occurred immediately after the start-up of the Talbot capturing device 61. Thus, if artifacts caused by moire stripes are noticed in the image, e.g., absorption image, at an intolerable level, the background image can be recaptured to obtain a new BG moire image Mb. In such a case, the new BG moire image Mb is used in the subsequent capturing operations performed by the Talbot capturing device 61. Alternatively, the distortion in the first grating 66 and the second grating 67 can be confirmed through comparison of a BG moire image Mb acquired, for example, through background capturing performed at a predetermined timing without a subject and the BG moire image Mb captured immediately after start-up of the Talbot capturing device 61.

In a reconstruction process, pixel values of the absorption image, differential phase image, and small-angle scattering image are calculated from all image signals of the moire images Mo containing the subject and all BG signals of the BG moire images Mb containing the background, so as to reconstruct and generate the absorption image and other images as described below. Hereinafter, the image signal corresponding to each pixel (i.e., each transducer in the X-ray detector 68 (the same applies hereinafter)) in a moire image Mo containing a subject is denoted by $I_S(x,y)$, and the BG signal corresponding to each pixel in a BG moire image Mb containing the background is denoted by $I_{BG}(x,y)$.

The image signal $I_S(x,y)$ and the BG signal $I_{BG}(x,y)$ can each be resolved and approximated by at least the DC component $I_0$ and primary amplitude component $I_1$ of the moire stripes:

$$I_S(x,y,k)=I_0(E_{S0},x,y)+I_1(E_{S1},x,y)\times \cos 2\pi(y\theta/d_2+\zeta\phi_X(E_{S1},x,y)+k/M) \qquad (1)$$

$$I_{BG}(x,y,k)=I_0(E_{BG0},x,y)+I_1(E_{BG1},x,y)\times \cos 2\pi(y\theta/d_2+k/M) \qquad (2)$$

where x and y are the coordinates indicating the position of each pixel, M is the number of fringe scanning operations, 1/M is the pitch of the grating movement in one fringe scanning operation, and k is a signal at the k-th grating position.

$E_{S0}$ and $E_{BG0}$ are values representing the energy spectrum of the X-ray beams passing through the gratings and the subject, and the energy spectrum of the X-ray beams passing through only the gratings, respectively, e.g., averages or peak values of energy of the X-ray beams passing through. $E_{S1}$ and $E_{BG1}$ are energy values representing the amplitude of moire stripes, and are determined by the energy spectrum of the X-ray beams passing through the gratings and the subject and the energy spectrum of the X-ray beams passing through only gratings, respectively, and the designed value of energy determined based on the thickness and positions of the gratings. $\theta$ is the relative angle between the grating directions of the first grating 66 and the second grating 67, $d_2$ is the pitch d of the second grating 67, as described above (see FIG. 9), $\zeta$ is a factor determined by the gratings and their positions, and $\phi_X$ is the angle of refraction of X-ray beams at the subject.

If the image signal $I_S(x,y)$ and the BG signal $I_{BG}(x,y)$ are expressed as above, the pixel values $I_{AB}(x,y)$, $I_{DP}(x,y)$, and $I_V(x,y)$ of an absorption image $I_{AB}$, a differential phase image $I_{DP}$, and a small-angle scattering image $I_V$, respectively, are calculated as follows:

$$I_{AB}(x,y)=I_0(E_{S0},x,y)/I_0(E_{BG0},x,y) \qquad (3)$$

$$I_{DP}(x,y)=(y\theta/d_2+\zeta\phi_X(E_{S1},x,y)-y\theta/d_2))/\zeta \qquad (4)$$

$$\therefore I_{DP}(x,y)=\phi_X(E_{S1},x,y) \qquad (5)$$

$$I_V(x,y)=(I_1(E_{S1},x,y)/I_0(E_{S0},x,y))/(I_1(E_{BG1},x,y)/I_0(E_{BG0},x,y)) \qquad (6)$$

In the reconstruction process described above, at least an absorption image $I_{AB}$, a differential phase image $I_{DP}$, and a small-angle scattering image $I_V$ are reconstructed and generated from image signals of the moire images Mo containing the subject and BG signals of the BG moire images Mb containing the background. These images can be combined to generate a new image. In this embodiment, five types of diagnostic medical images are generated, i.e., the three types of diagnostic medical images described above, and two types of combined images $I_E$ and $I_F$; where the combined image $I_E$ is derived from calculating and combining (absorption image $I_{AB}$)+(small-angle scattering image $I_V$) of every pixel, and the combined image $I_F$ is derived from calculating and combining (differential phase image $I_{DP}$)−(absorption image $I_{AB}$) of every pixel.

Characteristic Configurations of this Embodiment

A diagnostic medical image system including both the first capturing units 50 and the second capturing units 60, for example, as a result of introduction of the second capturing units 60 to a diagnostic medical image system already including the first capturing units 50 and the consoles 90, may not be able to appropriately correlate the processed diagnostic medical images p at the consoles 90 to the corresponding capturing order information, as described above.

That is, as described above, a console 90 of a general-purpose first capturing unit 50 links a diagnostic medical image generated from image signals D read by the FPD 1 to a single piece of capturing order information, so as to establish their 1:1 relationship. The console 90 should be operated to link the capturing order information with all images, e.g., the absorption image, the differential phase image, and the small-angle scattering image, reconstructed from the image signals D corresponding to the multiple moire images sent from the second capturing unit 60 including a Talbot capturing device 61.

The console 90 for the first capturing unit 50 links a diagnostic medical image and a single piece of capturing order information, so as to establish their 1:1 relationship. Thus, the console 90 may link only the first reconstructed medical image, e.g., the absorption image among the several types of diagnostic medical images reconstructed from the image signals D corresponding to the moire images sent from the Talbot capturing device 61, to the corresponding capturing order information. This prevents other images, such as the differential phase image and the small-angle scattering image, from being linked to the capturing order information.

If the console 90 is operated to link the several types of diagnostic medical images to a single piece of capturing order information so as to avoid this drawback, when image signals D of a single diagnostic medical image is sent through an X-ray capturing operation performed by the first capturing unit 50 for general capturing, the console 90 is operated to generate the single diagnostic medical image from the image signals D to be linked to the capturing order information but determines that other diagnostic medical images remain to be linked to the capturing order information. Thus, the capturing process does not end. A diagnostic medical image system including both the first capturing unit 50 for general capturing and the second capturing unit 60 including the Talbot capturing device 61 has the problem described above, unless provided with an appropriate configuration.

Many different configurations can prevent such a problem. In this embodiment, the second capturing unit 60 includes a controller 80 that rectifies the data acquired at the second capturing unit 60 and sends the rectified data to the console 90, as illustrated in FIG. 1. In this embodiment, the controller 80 may be provided in the form of a computer, similar to that serving as the console 90, or a dedicated device. FIG. 1 illustrates a controller 80 installed in the front room of the capturing room Ra containing the second capturing unit 60. If multiple capturing rooms Ra contain second capturing units 60, controllers 80 are installed in the front rooms Rb of the capturing rooms Ra. Alternatively, the controllers 80 may be installed inside the capturing rooms Ra.

The configuration of a diagnostic medical image system 100 according to this embodiment (see FIG. 1) including first capturing units 50, second capturing units 60, consoles 90, and controllers 80, which are described above, will now be described. The operation of the diagnostic medical image system 100 according to this embodiment will also be described.

Although redundant descriptions are omitted, in this embodiment, X-ray capturing operations based on the capturing order information performed by the second capturing units 60, in addition to the first capturing units 50, can be assigned through capturing order information (see FIG. 4). For example, X-ray by the second capturing unit 60 in accordance with the capturing order information can be determined through selection of cartilage in a pop-up icon (not shown) retrieved from the "captured site" P7 column, selection of the second capturing unit 60, i.e., the Talbot capturing device 61, in a pop-up icon (not shown) retrieved from the "bucky device ID" P9 column, or assignment of the second capturing unit 60 in an additional column through character input or selection of a checkbox.

An X-ray capturing operation by the second capturing unit 60, i.e., X-ray capturing of a joint region or by the Talbot capturing device 61, can be assigned through the capturing order information, as described above. Alternatively, new capturing order information can be created at the console 90 to assign the X-ray capturing operation with the second capturing unit 60. Alternatively, the X-ray capturing operation with the second capturing unit 60 can be selected at the console 90. That is, for example, an operator or radiologist can operate an input unit (selection unit), such as a mouse, to click to select one of the displayed items "first capturing unit" and "second capturing unit" appearing on the display 90a of the console 90, so as to perform an X-ray capturing operation with the selected unit. Presumed capturing of a region of interest, such as a joint, involves both general capturing and X-ray capturing with the second capturing unit 60 with focus on cartilage. Thus, if the number of categories of body regions in the RIS cannot be increased, a selection mode is preferred.

If capturing order information assigning X-ray capturing with the second capturing unit 60 is selected as described above, the console 90 is operated in connection with the capturing order information to display an icon I (not shown) representing X-ray capturing with the second capturing unit 60 on the display 90a. The icon I, for example, depicts a Talbot capturing device 61 or displays "Talbot" or "second capturing unit." If the operator or radiologist operates the console 90 to start capturing, the console 90 sends capturing order information assigning information including patient information, capturing conditions, and other information and a capturing request to the controller 80.

In this embodiment, several types of diagnostic medical images, e.g., an absorption image $I_{AB}$, a differential phase image $I_{DP}$, and a small-angle scattering image $I_V$, are generated at the controller 80, not at the console 90. In addition to this, two types of combined images $I_E$ and $I_F$ are generated in this embodiment, as described above. This provides five types of diagnostic medical images in total, from which the diagnostic medical images and combined images to be generated are selected.

In this embodiment, the diagnostic medical images, such as the absorption image $I_{AB}$, are reconstructed at the controller 80. Upon completion of capturing of the moire images Mo by the Talbot capturing device 61, all image signals of the moire images Mo are sent to the controller 80 via the relay 54 (see FIG. 1).

In this embodiment, the absorption image $I_{AB}$, the differential phase image $I_{DP}$, the small-angle scattering image $I_V$, and the combined images $I_F$ and $I_F$ are generated at the controller 80, not at the console 90. If these images are individually sent to the console 90, the console 90 links the image received first to the capturing order information so as to establish their 1:1 relationship, and the remaining images received thereafter are not linked to the capturing order information, as described above.

In this embodiment, the controller 80 generates the several types of diagnostic medical images, such as the absorption image $I_{AB}$, as described above, consolidates these images, and sends the consolidated images to the console 90. The several types of diagnostic medical images (i.e., the five types of diagnostic medical images according to this embodiment), for example, are consolidated by sequentially joining the images in a predetermined order to form a single data item or group. For example, each image may contain supplementary information indicating that the image is included in a data group. In such a case, for example, information on the number of consolidated diagnostic medical images can be written in the header of the consolidated diagnostic medical images. In this way, the console 90 can confirm the information in the headers of the diagnostic medical images to correctly reconsolidate the images into one group in a case of separate transmission of the images from the controller 80.

The console 90 receives the consolidated diagnostic medical images from the controller 80 and collectively links the consolidated images, which are in the form of a single piece of data or a data group, to a corresponding capturing order information to establish their 1:1 relationship, through a process identical to the above-described process of linking the diagnostic medical image captured by the first capturing unit 50 to capturing order information (so as to establish their 1:1 relationship). In this way, the console 90 can surely link the several types of diagnostic medical images sequentially joined in a predetermined order into the form of a single piece of data or group to the corresponding capturing order information. This certainly prevents the linking of only one or few of the several types of the diagnostic medical images to the capturing order information, which also causes the non-linking of the remaining diagnostic medical images to the capturing order information.

Similar to the process carried out to a single diagnostic medical image sent from the first capturing unit 50 (i.e., FPD 1), the console 90 is operated to carry out precise image processing, such as gradation processing, appropriate for the sites captured in the diagnostic medical images linked to the capturing order information and links the image to the capturing order information. The pre-processed diagnostic medical images may remain in connection with the capturing order information, or otherwise may be updated to the post-processed images.

The console 90 is operated by an operator or radiologist to confirm and save a single diagnostic medical image (captured by the first capturing unit 50) and several types of diagnostic medical images (captured by the second capturing unit 60) linked with capturing order information as described above, and sends the saved diagnostic medical images and the corresponding capturing order information to the PACS 200 (see FIG. 1). A medical doctor can instruct the PACS 200 to send necessary diagnostic medical images generated as described above to a diagnostic terminal (not shown) for display, and examine the generated diagnostic medical images for diagnosis.

[Advantageous Effects]

As described above, a diagnostic medical image system 100 according to this embodiment includes both a first capturing unit 50 for general capturing and a second capturing unit 60 including a Talbot capturing device (i.e., a Talbot capturing device including a Talbot or Talbot-Lau interferometer) 61. A controller 80, not a console 90, generates several types of diagnostic medical images from image signals corresponding to several images read by the second capturing unit 60, consolidates the resulting several types of diagnostic medical images, and sends the consolidated images to the console 90. The controller 80 in the diagnostic medical image system 100 according to this embodiment consolidates the several types of diagnostic medical images (such as the absorption image and differential phase image) reconstructed from multiple moire images Mo captured by the second capturing unit 60 through multiple capturing operations into a single piece of data or group.

The console 90 receives the data or group and collectively links the several types of diagnostic medical images, which is consolidated into a single piece of data or, to a corresponding capturing order information to establish their 1:1 relationship, through a process identical to the above-described process of linking the diagnostic medical image captured through a general capturing operation to capturing order information (so as to establish their 1:1 relationship). This links the several types of diagnostic medical images in the form of a single piece of data or group to capturing order information. Thus, all of the several types of diagnostic medical images reconstructed from the moire images Mo captured through X-ray capturing performed by the second capturing unit 60 in accordance with the capturing order information can be correctly linked to the capturing order information.

In the diagnostic medical image system 100 according to this embodiment, the controller 80 consolidates or rectifies the several types of diagnostic medical images reconstructed at the second capturing unit 60 into a single piece of data or group, so that all data items sent from the first capturing unit 50 and the second capturing unit 60 to the console 90 are in the form of a single piece of data or group. In a diagnostic medical image system including both a first capturing unit 50 and a second capturing unit 60, for example, as a result of introduction of a Talbot capturing device 61 into a diagnostic medical image system including an FPD 1 for general capturing, the first capturing unit 50 captures a single diagnostic medical image and the second capturing unit 60 reconstructs several types of diagnostic medical images. A diagnostic medical image system having the configuration described above can correctly link the diagnostic medical image captured by the first capturing unit 50 and the several types of diagnostic medical images reconstructed by the second capturing unit 60 to the corresponding capturing order information.

This certainly prevents the linking of only one or few of the several types of diagnostic medical images reconstructed from the moire images Mo captured by the second capturing unit 60 to the capturing order information, which also causes the non-linking of the remaining diagnostic medical images, or the erroneous determination by the console 90 that other diagnostic medical images remain to be linked to the capturing order information in addition to the diagnostic medical image captured by the first capturing unit 50, so as to prevent the capturing process from not ending. Data on one diagnostic medical image captured by the first capturing unit 50, data on multiple moire images captured by the Talbot capturing device, and data on the several types of diagnostic medical images reconstructed and generated from such data coincide in the system. Thus, the data on the diagnostic medical image can be certainly prevented from being erroneously linked to unrelated capturing order information, or a diagnostic medical image captured by a general-purpose capturing system can be prevented from being erroneously linked to unrelated capturing order information that is already linked to several types of diagnostic medical images.

[Modification 1]

Consoles 90 and PACSs 200 included in conventional diagnostic medical image systems for general capturing are mostly configured to manage and display diagnostic medical images (and combined images if present (the same applies hereinafter)) having a normal gradation, e.g., a 12-bit gradation. Diagnostic terminals and dedicated terminals have been developed that can display diagnostic medical images having a high gradation of 16 bits, for example. Thus, the controller 80 may select between two modes for reconstruction and generation of several types of diagnostic medical images: a normal mode for generating a diagnostic medical image having a normal gradation, e.g., a 12-bit gradation, and a high-gradation mode for generating images in a higher gradation.

[Modification 1-1]

If the console 90 can process a normal 12-bit gradation, the controller 80 carries out WW/WC gradation processing to the diagnostic medical image generated in a normal 12-bit mode; DICOM processing is carried out to both diagnostic medical images generated in the normal mode and the high-gradation mode; and the diagnostic medical images generated in the normal mode and the diagnostic medical images generated in the high-gradation mode are respectively consolidated and sent to the console 90. As described above, the console 90 is operated to consolidate the several types of diagnostic medical images to be linked with capturing order information. The capturing order information can be duplicated, and the diagnostic medical image generated in the normal mode may be linked to one of the capturing order information and the diagnostic medical images generated in the high-gradation mode to the other capturing order information. In such a case, the two pieces of capturing order information are managed and treated separately.

Alternatively, the diagnostic medical image generated in the normal mode and the diagnostic medical image generated in the high-gradation mode can both be linked to a single capturing order information. In such a case, both the diagnostic medical image generated in the normal mode and the diagnostic medical image generated in the high-gradation mode are managed and treated in connection with the capturing order information. The console 90 can carry out precise image processing, such as gradation processing, depending on the captured site on both the diagnostic medical image generated in the normal mode and the diagnostic medical image generated in the high-gradation mode, save these diagnostic medical images, and send all of the diagnostic medical images to the PACS 200. In this way, a medical doctor can instruct a conventional diagnostic terminal to retrieve a diagnostic medical image generated in the normal mode (e.g., 12-bit mode) from the PACS 200 and display the image on the diagnostic terminal, and also, instruct a new diagnostic terminal or dedicated terminal that can display images having a high gradation, e.g., a 16-bit gradation, to retrieve a diagnostic medical image generated in the high-gradation mode from the PACS 200 so as to observe the diagnostic medical image displayed in a high gradation.

[Modification 1-2]

If the console 90 can only process image data conforming to a normal 12-bit gradation and is unable to process image data having a high gradation, e.g., 16-bit gradation, the controller 80 can consolidate only the diagnostic medical images generated in the normal mode among the diagnostic medical images generated in the normal and high-gradation modes and send the consolidated images to the console 90. In such a case, the console 90 receives the diagnostic medical images generated in the normal mode to be linked with the capturing order information, carries out precise image processing, such as gradation processing, in accordance with the site captured in the diagnostic medical images, and sends the saved diagnostic medical images together with the capturing order information to the PACS 200. A medical doctor can observe the diagnostic medical image generated in the normal mode (e.g., a 12-bit gradation) by instructing the PACS 200 to send the diagnostic medical image generated in the normal mode to a diagnostic terminal for display.

The controller 80 can also generate several types of diagnostic medical images in the high-gradation mode, carry out precise image processing, such as gradation processing, in accordance with the site captured in the diagnostic medical images, and output the processed diagnostic medical images to a predetermined storage medium, such as a USB memory. The predetermined storage medium can be connected to a dedicated terminal that can display images in a high gradation, e.g., 16-bit gradation, so as to display the diagnostic medical image in a high gradation. In this way, even if image data having a high gradation, e.g., 16-bit gradation, cannot be processed at the console 90 that only can process image data having a normal gradation, e.g., 12-bit gradation, a medical doctor can connect the predetermined storage medium storing the several types of diagnostic medical images generated in the high-gradation mode to a dedicated terminal so as to display and observe the diagnostic medical image generated in the high-gradation mode and having a high gradation.

[Modification 2]

In the embodiment described above, the controller 80, for example, is in the form of a desktop computer installed in the front room Rb of the capturing room Ra. Alternatively, the controller 80 may be in the form of a portable terminal (not shown), such as an iPad (trademark). In such a case, the controller 80 in the form of a portable terminal is carried by the operator or radiologist. The operator instructs the controller 80 in the form of a portable terminal to retrieve the image signals corresponding to the multiple moire images Mo captured by the second capturing unit 60 from the Talbot capturing device 61 through wireless communication.

A process similar to that described above can be carried out by the controller 80 to consolidate the several types of diagnostic medical images and send the consolidated images to the console 90 through wireless communication (as in the embodiment described above), the several types of diagnostic medical images generated in both the normal mode and the high-gradation mode can be consolidated and sent to the console 90 (as in Modification 1-1), or the several types of diagnostic medical images generated at the controller 80 in the form of a portable terminal in the high-gradation mode can be output to a predetermined storage medium (as in Modification 1-2). If Modification 2 is applied to Modification 1-2, the controller 80 in the form of a portable terminal can be used as a predetermined storage medium. In such a case, the controller 80 in the form of a portable terminal can send information on the several types of diagnostic medical images to a dedicated terminal that can display images in a high gradation, e.g., a 16-bit gradation, so as to display the diagnostic medical images in a higher gradation.

According to Modification 2, the operator or radiologist can operate the controller 80 in the form of a portable terminal in hand to instruct the Talbot capturing device 61 of the second capturing unit 60 to send image signals corresponding to multiple moire images Mo to the controller 80, without actually going to the capturing room Ra containing the second capturing unit 60, as in the embodiment described above, so as to carry out the processes described above through the controller 80. Thus, the diagnostic medical image system 100 is easy to use by the operator.

Second Embodiment

In the first embodiment, the controller 80 (see FIG. 1) reconstructs and generates several types of diagnostic medical images from image signals corresponding to multiple moire images Mo captured by the second capturing unit 60, and the several types of diagnostic medical images are consolidated into a single piece of data or group and sent from the controller 80 to the console 90. Alternatively, the console 90 can reconstruct and generate several types of diagnostic medical images from the image signals of multiple moire images Mo captured through multiple capturing operations. In such a case, the console 90, which reconstructs and generates the several types of diagnostic medical images, can correctly link the resulting diagnostic medical images to capturing order information.

During transmission of the image signals corresponding to the multiple moire images Mo used in reconstruction of the several types of diagnostic medical images from the second capturing unit 60 to the console 90, both image signals corresponding to one diagnostic medical image captured by the first capturing unit 50 and image signals corresponding to the multiple moire images Mo captured by the second capturing unit 60 are present in the system. Thus, the image signals corresponding to multiple moire images Mo may be erroneously linked to capturing order information, or unrelated image signals corresponding to a diagnostic medical image captured by the first capturing unit 50 might be included in the image signals corresponding to multiple moire images Mo corresponding to the capturing order information.

To prevent such incidents, a controller 80 (see FIG. 1) for the second capturing unit 60 may be provided so as to consolidate the image data, rectify the consolidated image data, and send the rectified data to the console 90. In such a case, the controller 80 consolidates the image signals corresponding to the multiple moire images Mo read by the second capturing unit 60 and sends the consolidated image signals to the console 90, unlike the first embodiment described above. In this embodiment, the controller 80 does not reconstruct several types of diagnostic medical images from image signals corresponding to multiple moire images No captured through multiple capturing operations and does not combine the reconstructed images, unlike the first embodiment.

The console 90 receives image signals corresponding to one diagnostic medical image from the first capturing unit 50 (i.e., FPD 1), generates one diagnostic medical image from the received image signals, as described above, and links the resulting diagnostic medical image to the corresponding capturing order information. The console 90 receives consolidated image signals corresponding to multiple images from the controller 80, temporarily links the consolidated images to capturing order information, for example, reconstructs and generates an absorption image $I_{AB}$, a differential phase image $I_{DP}$, and a small-angle scattering image $I_V$ from the image signals corresponding to multiple images, and combines the reconstructed images to generate predetermined combined images $I_E$ and $I_F$. The console 90 is operated to link the generated diagnostic medical images to the corresponding capturing order information to display the resulting several types of diagnostic medical images on the display 90*a* (see FIG. 1). The operator or radiologist confirms and saves the displayed images, and the information on the images are sent to the PACS 200.

[BG Moire Image]

If multiple BG moire images Mb not containing a subject are captured when a background image is captured immediately after start-up of the Talbot capturing device 61 or when a background image is recaptured, the controller 80 consolidates the image signals corresponding to the captured BG moire images Mb and sends the consolidated image signals to the console 90, as described above. The console 90 reuses the BG moire images Mb that are received when the Talbot capturing device 61 is started up or when the background image is recaptured, in subsequent capturing performed by the second capturing unit 60. If a BG moire image Mb is captured every time the second capturing unit 60 performs an X-ray capturing operation, the controller 80 consolidates the image signals corresponding to multiple moire images Mo read by the second capturing unit 60 and the image signals corresponding to the multiple BG moire images Mb, and sends the consolidated signals to the console 90.

[Advantageous Effects]

As described above, the diagnostic medical image system 100 according to this embodiment includes both the first capturing unit 50 for general capturing and the second capturing unit 60 including the Talbot capturing device (i.e., Talbot capturing device including a Talbot or Talbot-Lau interferometer) 61, and the controller 80 consolidates the image signals corresponding to multiple images read by the second capturing unit 60 into a single piece of data or group and sends this to the console 90. Thus, mixing of the image signals corresponding to a single diagnostic medical image captured by the first capturing unit 50 with the image signals corresponding to the multiple moire images Mo captured by the second capturing unit 60 is certainly prevented. Thus, the advantageous effects described in the first embodiment can all be achieved.

In this embodiment, unlike the first embodiment, every time the console 90 generates the several types of diagnostic medical images (including combined images), the resulting diagnostic medical images can be displayed on the display 90*a* (see FIG. 1) of the console 90, for example, and the operator or radiologist can confirm the displayed images. This meets the demand of early viewing of the generated diagnostic medical images by the operator, and the time from the X-ray capturing at the second capturing unit 60 to the confirmation of all diagnostic medical images by the operator can be reduced. These features also provide a diagnostic medical image system 100 easy to use by the operator. Data (diagnostic medical image according to the first embodiment, and image signals corresponding to the moire images Mo according to the second embodiment) transmitted from the controller 80 to the console 90 in the first and second embodiments can be appropriately processed through lossless compression, for example.

[Modification 3]

According to the first and second embodiments, an absorption image $I_{AB}$, a differential phase image $I_{DP}$, and a small-angle scattering image $I_V$ are reconstructed and generated from image signals corresponding to multiple moire images Mo captured through multiple capturing operations performed by the second capturing unit 60, and two types of combined images $I_E$ and $I_F$ are generated, so as to generate five types in total of diagnostic medical images. In these cases, the diagnostic medical images and combined images to be generated from the image signals corresponding to the multiple moire images Mo are preassigned. Alternatively, the operator or radiologist may appropriately determine through the controller 80 in the first embodiment or the console 90 in the second embodiment which diagnostic medical images and combined images are to be generated from the image signals corresponding to the multiple moire images Mo captured through multiple capturing operations.

In the first embodiment, the several types of diagnostic medical images and the combined images are consolidated by the controller 80 and are sent to the console 90 as a single piece of data or group. Thus, other diagnostic medical images do not mix into the data item or group. In the second embodiment, the operator or radiologist instructs the console 90 to generate the several types of diagnostic medical images and the combined images, and then manually links the diagnostic medical images to the corresponding capturing order information while confirming the absence of other diagnostic medical images in the several types of diagnostic medical images. In this case also, the operator can determine the order of generation of the diagnostic medical images and combined images at the console 90, for example, and then the console 90 can operate so as to automatically generate the assigned images to be linked to the capturing order information.

Third Embodiment

As described above, if image signals corresponding to the multiple moire images Mo captured by the second capturing unit 60 through multiple capturing operations are sent to the console 90, image signals corresponding to other diagnostic medical images may be mixed into these image signals and cause confusion in the linking of the diagnostic medical images and capturing order information. In the second embodiment, the image signals corresponding to the multiple moire images Mo captured by the controller 80 through multiple capturing operations are consolidated into a single piece of data or group and sent to the console 90.

If the image signals corresponding to the moire images Mo sent from the second capturing unit 60 to the console 90 are image signals corresponding to one moire image Mo, image signals corresponding to a single image are sent from both the first capturing unit 50 (i.e., FPD 1) and the second capturing unit 60 to the console 90 without rectification at the controller 80. Thus, if the console 90 temporarily links the received image signals corresponding to one diagnostic medical image to the capturing order information, the diagnostic medical image generated from the image signals corresponding to one image (one type generated at the first capturing unit 50 and several types generated at the second capturing unit 60) can be linked to the capturing order information without error.

The Talbot capturing device (i.e., an X-ray capturing device including a Talbot or Talbot-Lau interferometer or involving Fourier transform) to be introduced into a diagnostic medical image system for general capturing (i.e., a diagnostic medical image system including only a first capturing unit 50) installed in a medical facility, such as a hospital, may be a non-scanning X-ray capturing device involving Fourier transform that reads image signals corresponding to one moire image Mo with an X-ray detector 68 irradiated once with X-ray beams irradiated from an X-ray source 62 and passing through a subject and multiple gratings 66 and 67. In such a case, the first grating in the X-ray capturing device involving Fourier transform may be a one-dimensional grating, such as that illustrated in FIG. 9, or a two-dimensional grating such as that disclosed in Patent Literature 7 mentioned above.

Even if the diagnostic medical image system 100 includes both a general-purpose first capturing unit 50 including an FPD 1 and a second capturing unit 60 including a Talbot capturing device, as a result of introduction of a Talbot capturing device into a diagnostic medical image system for general capturing, the console 90 receives image signals corresponding to one image captured by one of the capturing units through each capturing operation. Thus, the console 90 can be operated to receive the image signals to be linked to the capturing order information so as to certainly establish their 1:1 relationship.

Even if the console 90 generates several types of diagnostic medical images, such as an absorption image $I_{AB}$ and a differential phase image $I_{DP}$, through Fourier transform, for example, performed on the image signals corresponding to one moire image Mo sent from the second capturing unit 60, erroneous linking of the diagnostic medical images to incorrect capturing order information due to the mixing of other diagnostic medical images can be certainly prevented, and the diagnostic medical images can be certainly linked to the correct capturing order information.

[Generating Small-Angle Scattering Image First in Second Capturing Unit and Displaying Image]

During capturing using any X-ray capturing device, such as a Talbot capturing device, the operator or radiologist usually observes the captured image or a preview of the image to determine whether the subject is appropriately captured in the image and whether the image should be recaptured. The Talbot capturing device 61 in the second capturing unit 60 captures moire images, as described above. Unfortunately, it is difficult to determine whether the subject is appropriately captured in the reconstructed and generated absorption image and differential phase image through simple observation of the moire images. Thus, the need for recapturing cannot always be readily and speedily determined.

A configuration of a Talbot capturing device 61 that can readily and speedily determine the need for recapturing after capturing will now be described.

As described above, the Talbot capturing device 61 captures one or more moire images having distorted moire stripes appearing in the image of the subject. As described above, the operator or radiologist should determine whether the subject is appropriately captured in the image and determine the need for recapturing. Unfortunately, the appropriate image of the subject cannot be readily determined through simple observation of the moire images. Thus, an absorption image and other images should be reconstructed and generated from the moire images, and the need for recapturing should be determined through observation of these reconstructed images.

If the subject moves during capturing by the Talbot capturing device 61, in particular, the image quality of the images reconstructed and generated from the moire images, such as the absorption image, the differential phase image, and the small-angle scattering image, may decrease and the images may be unusable by a medical doctor for diagnosis. Such a movement of the subject during capturing requires recapturing of the subject. However, the movement of the subject during capturing cannot be determined through simple observation of the moire images. Thus, an absorption image and other images should be reconstructed and generated from the moire images, and the resulting images should be observed to determine whether the subject moved so as to determine the need for recapturing.

Figure 12:
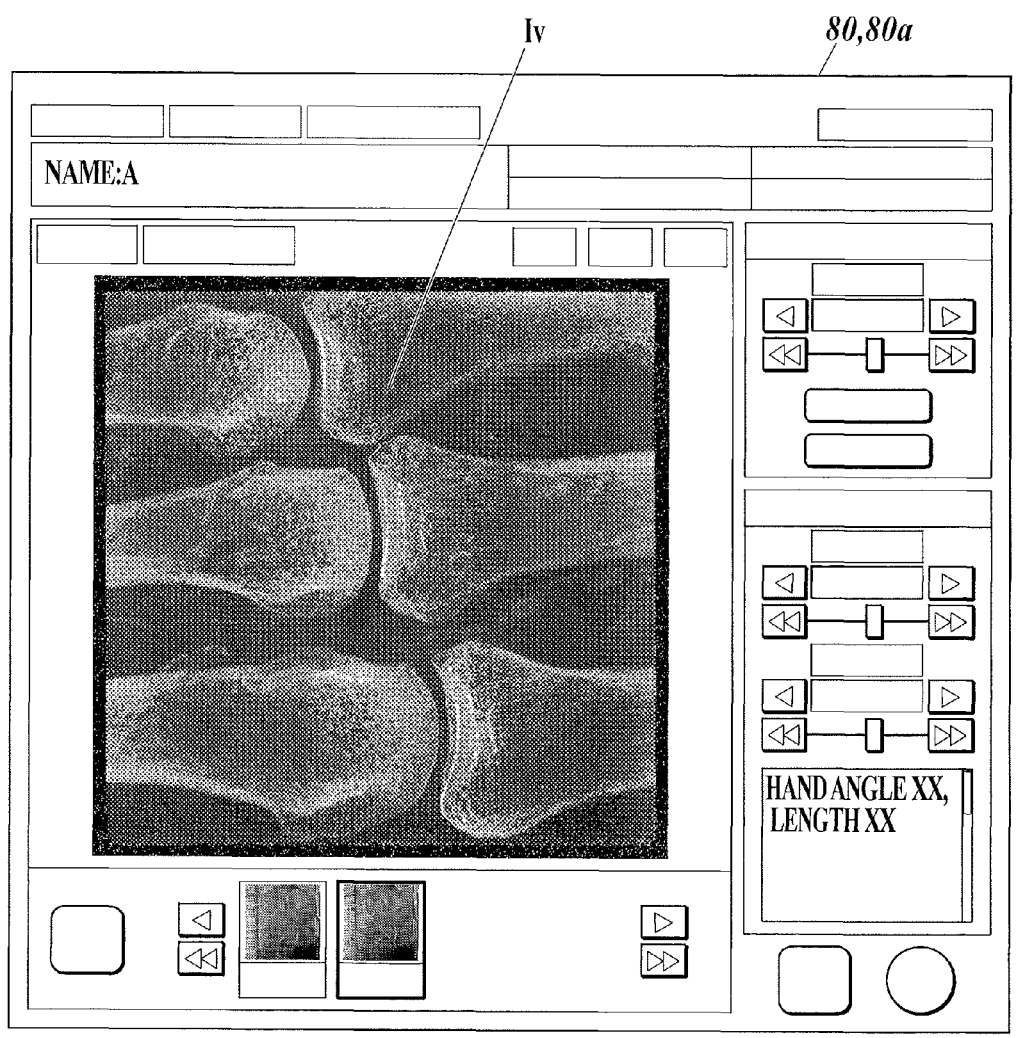
FIG. 12 illustrates an example small-angle scattering image displayed at the beginning on a display unit of a controller.

Actually, only extremely skilled radiologists can readily determine whether the subject moved during capturing through observation of an absorption image and a differential phase image. The inventors have conducted extensive research and discovered that small-angle scattering images among the reconstructed images have the best visibility concerning the movement of the subject. FIG. 12 illustrates an example small-angle scattering image $I_V$ reconstructed and generated from moire images capturing the joint regions of fingers. The small-angle scattering image $I_V$ has the highest visibility concerning movement of the subject during capturing among the reconstructed images because of the presumed reasons described below.

As described above, the small-angle scattering image $I_V$ captures a decrease in visibility of the moire stripes caused by the subject. The signals are characterized by their weakening in regions containing minute structure, e.g., edges of bone or trabecula. If the subject moves, false images may be generated due to an increase in small-angle scattering signals at the edge of the structure. The number of false images increases as the scale of the movement increases. That is, the small-angle scattering signals appear to increase at the edges of the structure. Thus, it is presumed that the operator or radiologist can readily and accurately determine a movement of the subject during capturing through observation of the generation of false images in the generated small-angle scattering image $I_V$ (i.e., whether false images are formed in the small-angle scattering image $I_V$). False images can be relatively readily confirmed by inexperienced radiologists. Thus, even an inexperienced operator or radiologist can readily determine the movement of the subject during capturing through visible observation.

Movement of the subject during capturing decreases the sharpness of an absorption image. The movement of the subject and the level of influence of the movement of the subject on the other reconstructed images, e.g., small-angle scattering image, are difficult to determine through observation of the absorption image with low sharpness even for experienced radiologists. Movement of a subject causes false images in signals at the edges of the structure in a differential phase image, similar to that in a small-angle scattering image. In a differential phase image, even if false images are not generated, the intensity (brightness) of the signals varies relatively greatly at the edges of the structure (e.g., the edge of a bone) (for example, see the differential phase image $I_{DP}$ in FIG. 9 described below). Thus, even if false images are generated due to movement of the subject, only experienced radiologists are able to readily determine the images as false images. In contrast, the movement of the subject during capturing can be readily confirmed on a small-angle scattering image $I_V$ through visible observation, as described above.

The controller 80 of the Talbot capturing device 61 (see FIG. 1) receives information on the moire images captured by the X-ray detector 68, as described above, and reconstructs and generates at least three types of reconstructed images, i.e., an absorption image, a differential phase image, and a small-angle scattering image, from the received information. Among the three types of reconstructed images, the controller 80 may first reconstruct and generate a small-angle scattering image $I_V$ and display the generated small-angle scattering image $I_V$ on a display 80a (see FIG. 12).

This configuration allows an inexperienced operator or radiologist to observe the displayed small-angle scattering image $I_V$ and readily determine the movement of the subject during capturing, which is difficult to determine through observation of an absorption image or a differential phase image, and thus readily determine the necessity of recapturing of the images. Displaying the small-angle scattering image $I_V$ first prior to the absorption image and the differential phase image allows speedy determination, and thus, the necessity of recapturing of the images can be readily and speedily determined after capturing of the moire images. The patient of interest continues to be fixed on the fastening device, for example, after the capturing of the moire images in preparation of possible recapturing. The configuration described above reduces the time required for the operator to determine the recapturing of the images, and if recapturing is necessary, the capturing operation can be immediately started. Thus, the burden on the patient can be reduced.

In order to immediately display the small-angle scattering image $I_V$ on the display 80a of the controller 80 after capturing, the controller 80 can generate a decimated moire image containing a reduced number of pixels compared to that in the original moire image captured by the X-ray detector 68, instead of generating a small-angle scattering image $I_V$ reconstructed from all values of the pixels in the original moire image captured by the X-ray detector 68 (if multiple moire images are captured, a decimated moire image is generated for every moire image through the same process). The controller 80 can first reconstruct and generate a small-angle scattering image $I_V^*$ based on the decimated moire image and display this on the display 80a. Through such a configuration, the small-angle scattering image $I_V^*$ can be immediately displayed on the display 80a of the controller 80 after capturing, and the operator or radiologist can speedily determine the necessity of recapturing of the images. The "*" sign in "small-angle scattering image $I_V^*$" indicates that the small-angle scattering image is generated from decimated moire images.

Along with the generation and display of small-angle scattering image $I_V^*$ based on decimated moire images, as described above, generation of the three types of reconstructed images based on original undecimated moire images can be carried out. Such a procedure can generate the reconstructed images more rapidly than generation of at least three types of reconstructed images after the determination of recapturing by the operator or radiologist, and thus, can reduce the time required from the start of capturing to the generation of the recaptured image.

In response to an instruction for recapturing input via an input unit, such as a mouse, by the operator or radiologist who observed the small-angle scattering images $I_V$ and $I_V^*$ and determined the recapturing of the images, the controller 80 discards the information on the original undecimated moire images and cancels the generation of the three types of images to be reconstructed from these moire images. This is because new moire images are to be captured by recapturing, and thus the original moire images are unnecessary and the generation of the three types of images to be reconstructed from the original moire images is unnecessary.

In the embodiment described above, at least three types of reconstructed images, i.e., an absorption image, a differential phase image, and a small-angle scattering image, are reconstructed and generated. Alternatively, the small-angle scattering image $I_V$ can be predominantly reconstructed, and after confirmation that there is no motion of the subject, the absorption image and the differential phase image may be reconstructed. If the small-angle scattering image $I_V^*$ is to be predominantly reconstructed, decimated moire images can be used as described above to reduce the time required for display of the small-angle scattering image $I_V^*$.

If the operator or radiologist determines that recapturing is not necessary (i.e., the operator inputs an instruction for confirmation or does not input an instruction for recapturing via an input unit within a predetermined time) through observation of the small-angle scattering images $I_V$ and $I_V^*$, the controller 80 is operated to consolidate and send the generated several types of diagnostic medical images (the absorption image, the differential phase image, and the small-angle scattering image) to the console 90, as described above. Alternatively, several types of diagnostic medical images may be consolidated without the determination by the operator and sent to the console 90, and if the operator inputs an instruction for recapturing, the controller 80 may instruct the console 90 to discard these diagnostic medical images.

As described above, small-angle scattering images $I_V$ and $I_V^*$ form false images if the subject moves during capturing and thus allow ready determination of a movement of a subject during capturing, compared to observation of absorption images and differential phase images. Thus, both experienced radiologists and inexperienced operators can observe the small-angle scattering images $I_V$ and $I_V^*$ displayed first so as to readily determine the movement of the subject during capturing, and readily determine the necessity of recapturing. Displaying the small-angle scattering images $I_V$ and $I_V^*$ first prior to the generated absorption image and the differential phase image allows ready determination, and thus, the necessity of recapturing can be readily and speedily determined after capturing of moire images.

The patient of interest continues to be fixed on the fastening device in preparation of recapturing even after the moire images are captured. The configuration described above reduces the time required by the operator to determine the necessity of recapturing, and if required, recapturing can be performed quickly. Thus, the burden on the patient is reduced.

According to the second embodiment described above, if the console 90 reconstructs and generates several types of diagnostic medical images based on image signals corresponding to multiple moire images Mo, the console 90 reconstructs and generates the small-angle scattering image $I_V$ first among at least three types of reconstructed images, i.e., an absorption image, a differential phase image, and a small-angle scattering image, and displays the generated small-angle scattering image $I_V$ on the display 90a (see FIG. 1). In such a case, also, the same advantageous effects as described above are achieved.

[Processes During Capturing with Talbot Capturing Device]

The processes during capturing with the Talbot capturing device 61 will now be described. Prior to capturing, before receiving a capturing request from the console 90, the controller 80 displays an instruction such as "waiting for order" on the display 80a (see FIG. 12) and enters a stand-by mode. The "order" refers to capturing order information (see FIGS. 4 and 5) sent from the console 90 to the controller 80, together with the capturing request.

Figure 13:
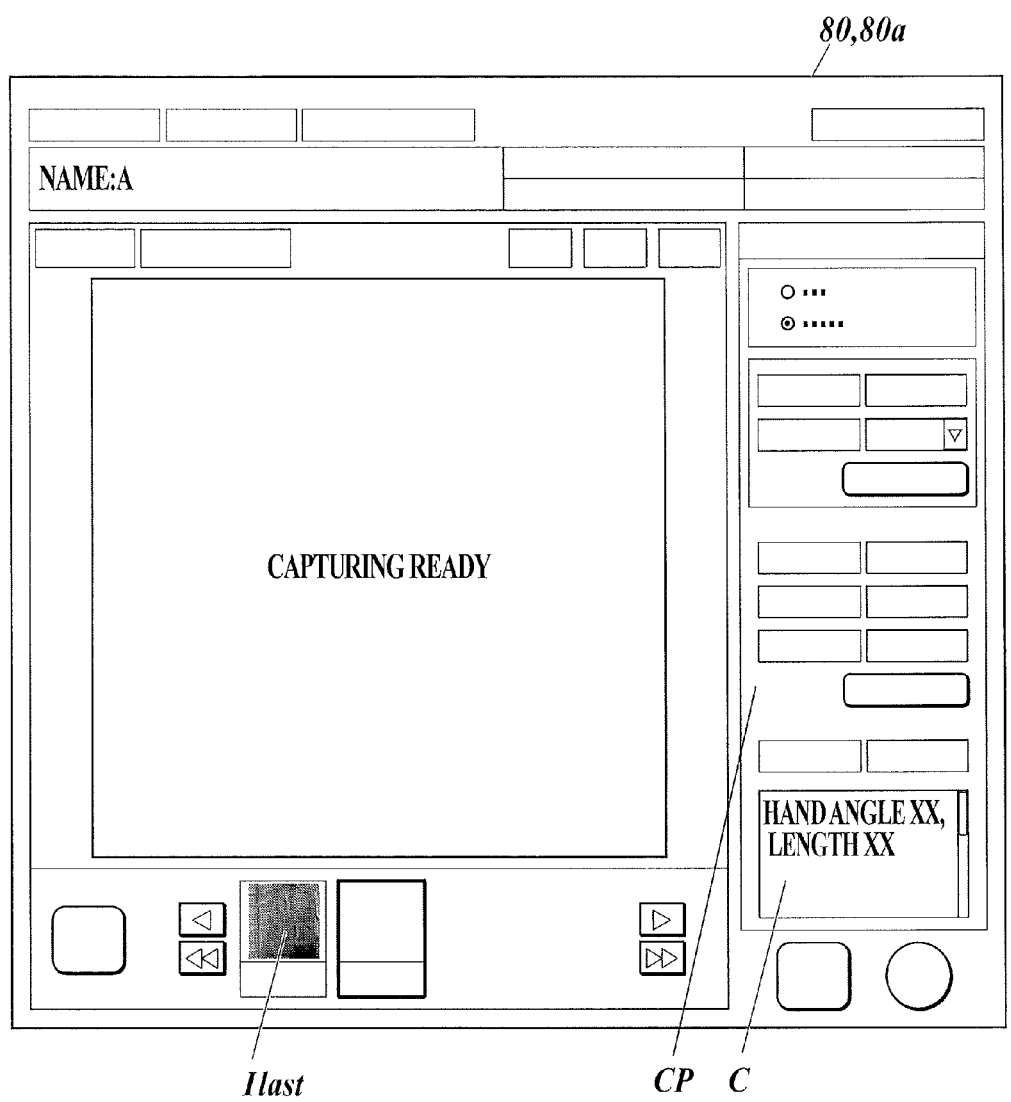
FIG. 13 illustrates an example stand-by screen displayed on the display unit of the controller.

Upon reception of the capturing order information and the capturing request from the console 90, the controller 80 changes the display on the display 80a to a stand-by screen, such as that illustrated in FIG. 13. In this embodiment, a control panel CP is displayed in the stand-by screen and allows setting of the tube voltage, the tube current, and the irradiation time. After the operator or radiologist establishes the tube voltage and the other parameters on the control panel CP, the controller 80 sends the information on the tube voltage and the other parameters directly to the X-ray source 62 of the Talbot capturing device 61 (see FIG. 8) or to a generator of the X-ray source 62, if the X-ray source 62 includes a generator.

The stand-by screen illustrated in FIG. 13 includes a display column C that displays information on parameters for the previous capturing operation performed on the patient assigned in the received capturing order information, which contains the angle and the traction length of the hand of the patient of interest set when the joint region of the hand is fixed with a fastening device (not shown). The operator or radiologist can review the parameters to fix the hand of the patient with the fastening device in accordance with the same parameters, i.e., position and traction length, as those for the previous capturing operation, and perform capturing under the same conditions as those of the previous capturing operation. The stand-by screen as shown in FIG. 13 displays, for example, an image $I_{last}$ reconstructed and generated during the previous capturing operation (for example, a differential phase image).

As described above, images of the background are captured immediately after the Talbot capturing device 61 is started up. The controller 80 receives and stores the BG moire images Mb containing the background in a storage device (not shown). In actual X-ray capturing, previous to the capturing, the subject fixed to the subject table 65 (see FIG. 8) of the Talbot capturing device 61 is irradiated once with a low dose of X-ray beams irradiated from the X-ray source 62 to confirm the positioning of the subject on the subject table 65 (which is a process known as preliminary capturing).

For example, when the body, e.g., hand or leg of the patient of interest is fixed with a fastening device and captured, before main capturing, the position and angle of the subject fixed with the fastening device should be appropriately adjusted. Thus, before the main capturing operation, the hand or leg of the patient fixed with the fastening device are placed on the subject table 65 of the Talbot capturing device 61 (see FIG. 8). The operator or radiologist adjusts the angle and traction length in accordance with the parameters for the previous capturing operation displayed in the display column C on the screen (see FIG. 13), and performs preliminary capturing. The preliminary capturing is continued after adjustment of the positions and angles of the hand and the lengths and forces of traction applied to the hand. The position and angle of the hand or leg of the patient of interest and the length and force of traction applied are hereinafter collectively referred to as the conditions of the captured site of the subject.

Figure 14:
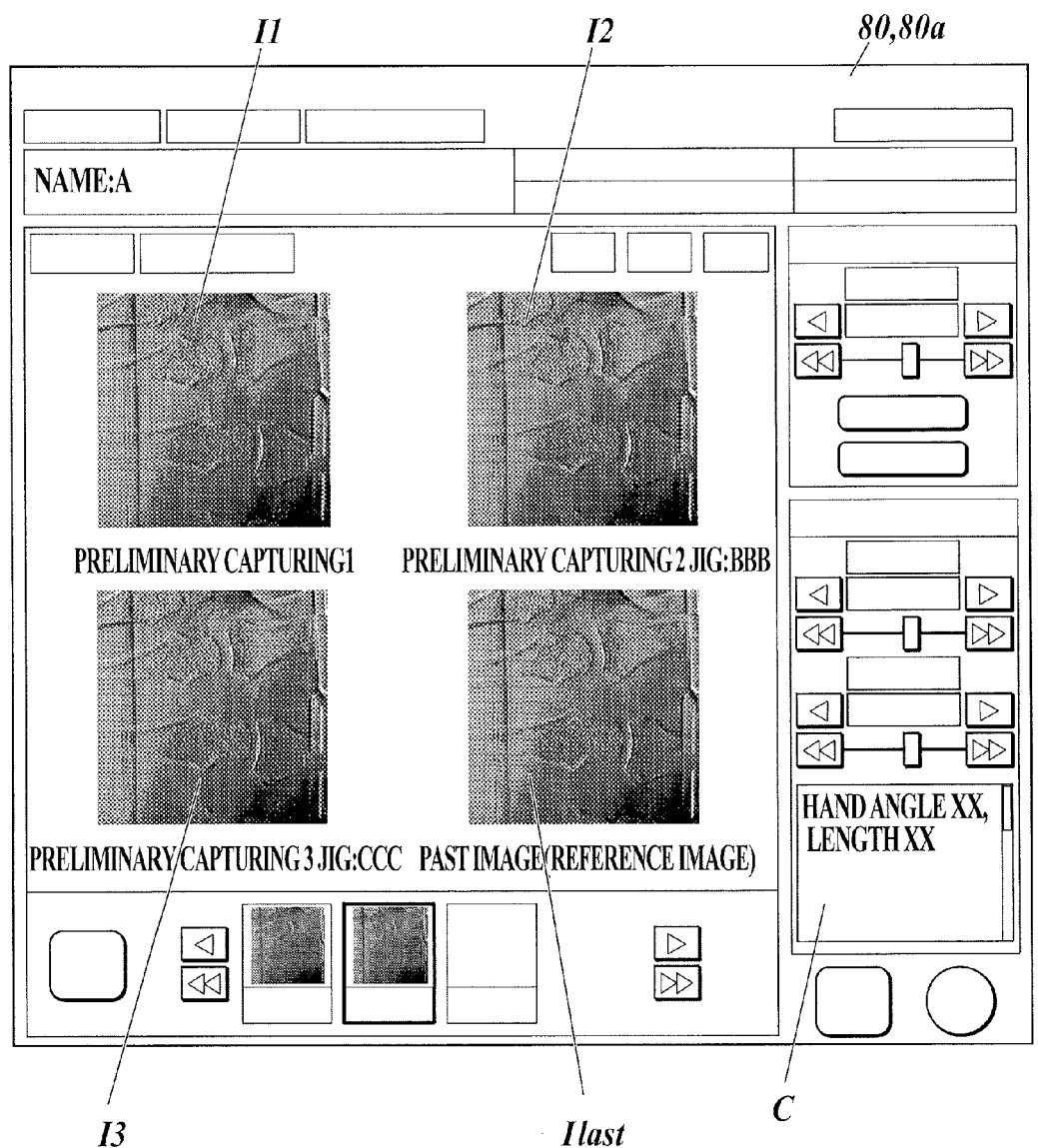
FIG. 14 illustrates an example screen displaying images of a subject captured by varying the conditions of the captured site and an image captured in the past.

The controller 80 generates images I, such as reconstructed images, from moire images (not shown) obtained during preliminary capturing while varying the conditions of the captured site of the subject, and displays the resulting images I on the screen, such as in FIG. 14. For example, as illustrated in FIG. 14, an image $I_{past}$ containing the site of the same subject (patient) captured in the past or, if an image of the same patient from the past is not available, a reference image (not shown) of the same captured site of a different patient can be displayed on the display 80a in addition to the images I (I1 to I3) obtained during preliminary capturing, for comparison. In this way, the images I obtained through preliminary capturing can be instantly compared with the image $I_{past}$ or reference image that appropriately captures a joint region of the patient from the past. The images can be compared to capture under conditions of the captured site of the subject, i.e., the position and angle of the hand or leg of the patient and the length and force of the traction of the hand or leg, most similar to the conditions of the captured site in the past image $I_{past}$, and the subject can be fixed with a fastening device to recreate these conditions. In this way, the joint region of the patient can be appropriately captured in the same way as in the past image $I_{past}$ captured in the past, and every capturing operation can be performed under the same conditions of the captured site of the subject. Thus, the subject can be readily observed over time for the progression and degree of wearing in the cartilage in the joint region, for example.

FIG. 14 illustrates four images, i.e., three reconstructed images I1 to I3 captured while varying the conditions of the captured site of the subject and an image $I_{past}$ captured in the past, are displayed in a 2×2 matrix. Alternatively, each image may be displayed in a frame-by-frame fashion, or may be scrolled for display. The images may be displayed in any display scheme.

The operator or radiologist may select each image I obtained through preliminary capturing and input information on the conditions of the captured site of the subject (i.e., the position and angle of the hand and the length and force of traction) in capturing. The controller 80 may link this information to the corresponding image I (i.e., add to the image as supplementary information). The information linked to the images can be displayed on the screen, and the operator or radiologist can confirm the displayed information while selecting the appropriate image I among the images I; that is, the operator or radiologist can adequately select the setting of the conditions of the captured site of the subject.

Every time the conditions of the captured site of the subject is varied during a preliminary capturing operation, the site of the subject and the fastening device may be captured with a camera (not shown), and the operator or radiologist may input the images of the site of the subject and the fastening device captured with the camera to the controller 80. In response, the controller 80 may link these images to the corresponding images I. In this way, the conditions of the captured site of the subject can be confirmed not only as parameters on the position and angle of the hand and the length and force of the traction, for example, but also as image information captured by the camera. Thus, the operator or radiologist can select an appropriate image I among the images I, as described above, while confirming the images captured by the camera, so as to adequately select the image I, that is, the setting of the captured site of the subject. In this way, depending on the positioning and the angle of view of the camera relative to the fastening device, the observer of the image can notice which (right or left) hand or leg is captured in the image on the basis of the relationship between the captured joint region and the entire body of the patient.

After an image I is selected among the multiple images I obtained through preliminary capturing, as described above, the controller 80 displays the information on the conditions of the captured site of the subject (i.e., information on the position and angle of the hand and the length and force of the traction, for example) and the camera image containing the conditions of the captured site of the subject in connection with the selected image I on the display 80a. For example, the information on the conditions of the captured site of the subject linked to the selected image I may be displayed in the display column C, or the camera image containing the conditions of the captured site of the subject may be displayed on the display 80a. The operator or radiologist can observe such information and set the captured site of the subject when the subject is fixed with the fastening device to be the selected conditions of the captured site of the subject.

[Processing Moire Images with Controller after Capturing]

The controller 80 receives information on moire images captured at the Talbot capturing device 61 and first reconstructs and generates a small-angle scattering image $I_V$ among the several types of diagnostic medical images (absorption image, differential phase image, and small-angle scattering image) to be reconstructed and generated from the information as described above, and displays the generated small-angle scattering image $I_V$ on the display 80a, as illustrated in FIG. 12. As described above, if the controller 80 generates a decimated moire image through decimation of the pixels in the moire image, a small-angle scattering image $I_V^*$ is first reconstructed and generated based on the decimated moire image and displayed on the display 80a.

Figure 15:
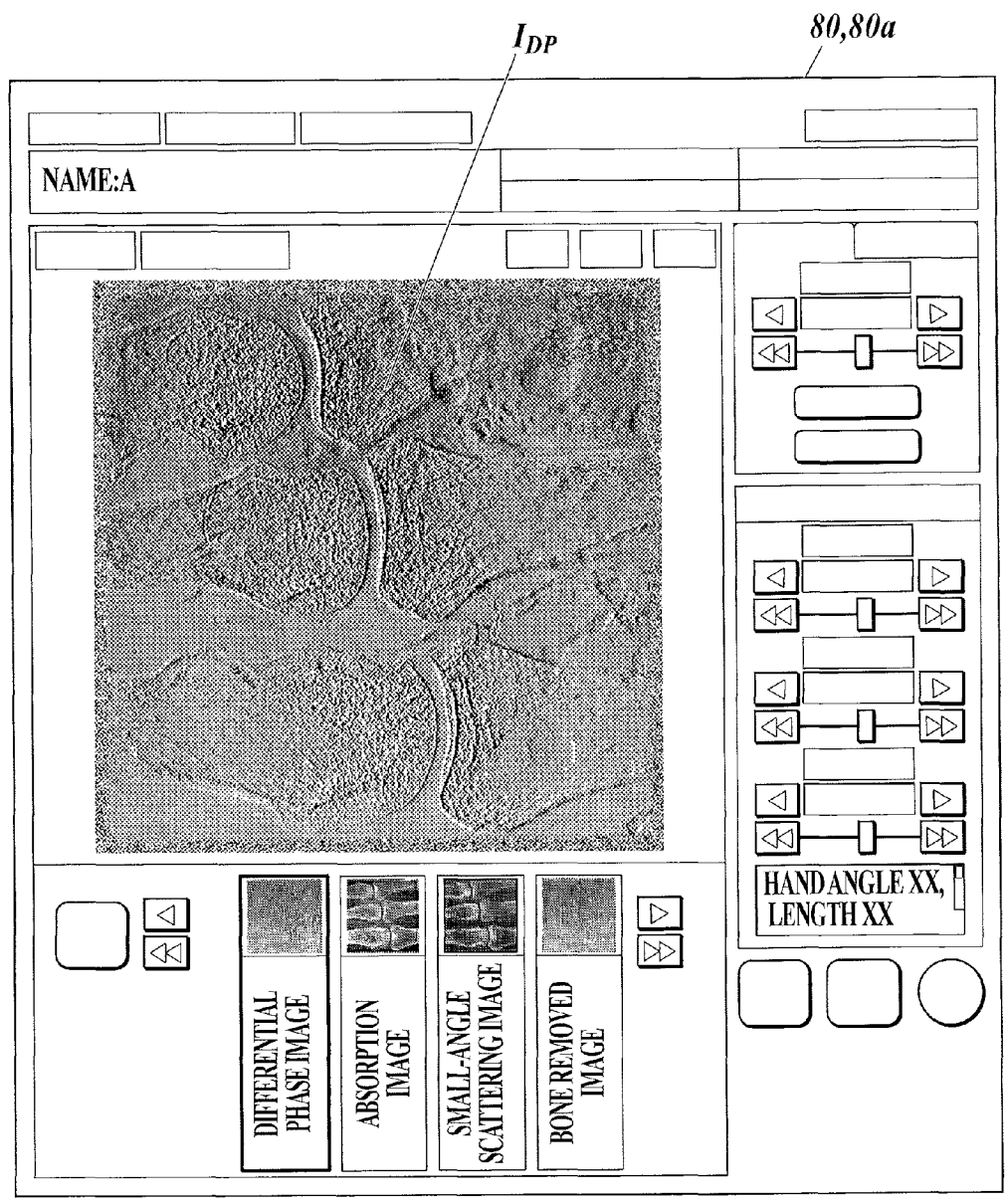
FIG. 15 illustrates an example differential phase image displayed on the display unit of the controller.

If the operator or radiologist confirms the small-angle scattering images $I_V$ and $I_V^*$ and then carries out an operation of confirmation (e.g., clicking on a button icon representing the confirmation) or the controller 80 displays the small-angle scattering images $I_V$ and $I_V^*$ on the display 80a, and then if the operator does not carry out any operation for a predetermined time, the controller 80 presumes that the small-angle scattering images $I_V$ and $I_V^*$ have been confirmed and generates a differential phase image $I_{DP}$ and displays the image on the display 80a, as illustrated in FIG. 15. This is because a differential phase image has the highest descriptiveness (visibility) for cartilage, which is the region of interest. If the entire joint region including cartilage is the region of interest, another reconstructed image, such as an absorption image $I_{AB}$, may be displayed first.

In some cases, even if a movement of the subject is noticed in the small-angle scattering images $I_V$ and $I_V^*$, diagnosis may be possible with a differential phase image $I_{DP}$, which has high descriptiveness for cartilage in the region of interest. In such a case, diagnosis of the differential phase image $I_{DP}$ is preferred to recapturing of the patient, which increases the exposed dose of the patient. In such a case, it is preferred that the differential phase image $I_{DP}$ is displayed after the capturing of the patient, and a known method of detecting movement (blurring of a subject in an image) using the small-angle scattering images $I_V$ and $I_V^*$ is simultaneously carried out so as to automatically detect movement of the subject. If movement of the subject is detected, the result should be superimposed on the edge region of the displayed differential phase image $I_{DP}$ as "movement detected," so that the operator or radiologist can cautiously determine whether the images should be used for diagnosis. If the operator or radiologist determines that the images can be used for diagnosis, the series of related images should be labeled to indicate the detection of the movement.

With reference to FIG. 15, thumbnails of the reconstructed images to be used for various types of diagnosis are displayed in the bottom region of the display 80a, and the thumbnail corresponding to the large image displayed in the central area of the screen is emphasized surrounded by a frame. The large image can be switched by scrolling through the thumbnails using a scrolling button to move the frame and assigning a thumbnail to be enlarged.

Figure 16:
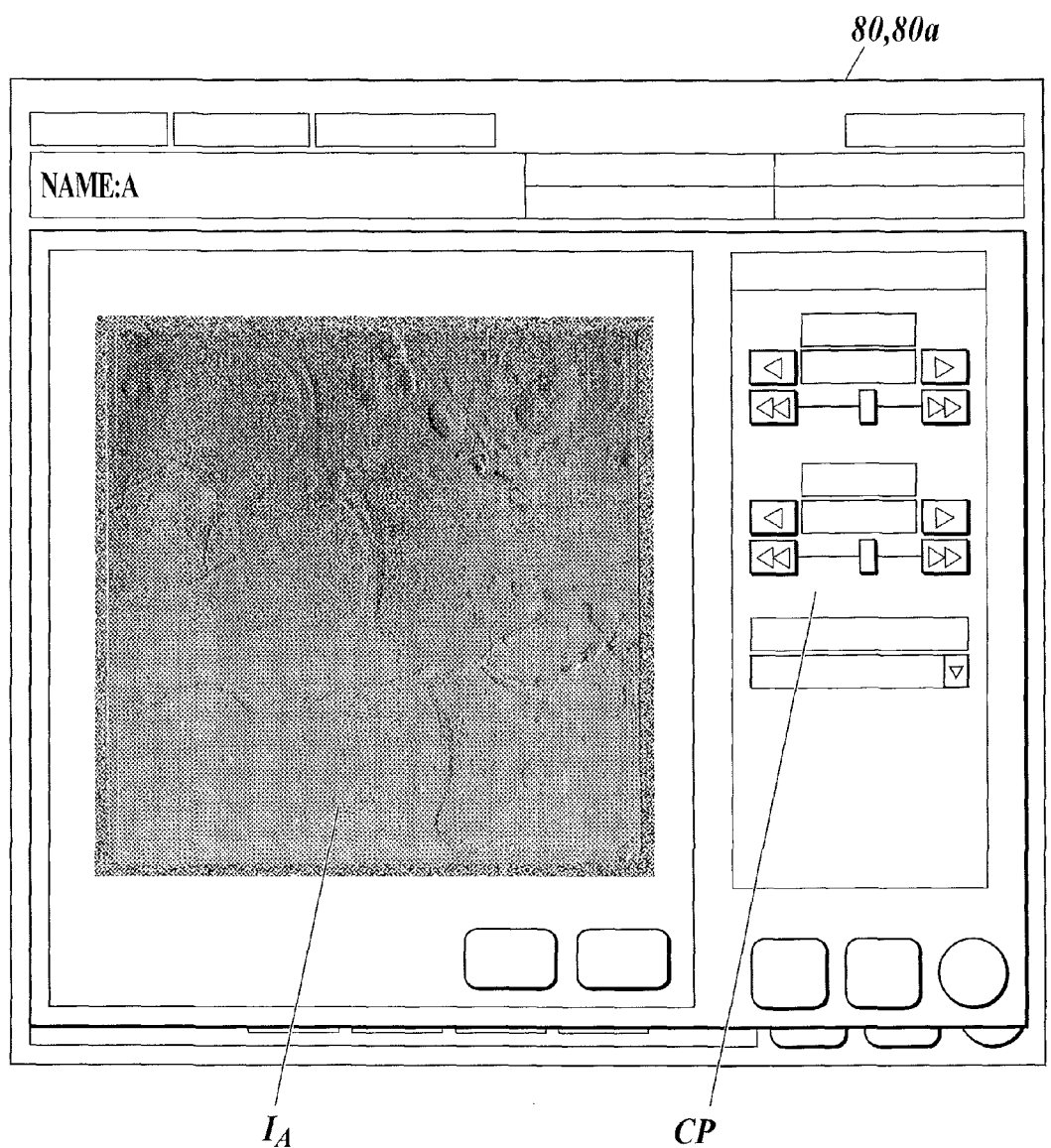
FIG. 16 illustrates an example bone removed image (soft-tissue differential image) generated from the differential phase image in FIG. 12.

With reference to FIG. 16, the controller 80 may reconstruct a new image $I_A$ after bone removal and display this on the display 80a. This bone removed image $I_A$ will now be described.

Among the reconstructed images, an absorption image visualizes structures such as bone with high sensitivity. The differential phase image $I_{DP}$ can visualize not only bone but also soft tissue such as cartilage, which is difficult to visualize in an absorption image. Unfortunately, if soft tissue such as cartilage and bone overlap in a differential phase image $I_{DP}$, it is difficult to visualize the soft tissue because bone has a more intense signal than that of soft tissue. For example, if the hand is captured without adjustment (i.e., without adjustment of the angles), the soft tissue and the bone frequently overlap in the resulting differential phase image $I_{DP}$. Such overlapping has been avoided through adjustment of the angle of capturing such that gaps are formed between the joints to be captured, and extending of the gaps during capturing. Unfortunately, the shape of fingers vary for each person, and in some cases, such adjustment cannot eliminate the overlapping of the soft tissue and the bone.

The inventors, who conducted extensive research, discovered that removal or subtraction of signals corresponding to bone in a differential phase image $I_{DP}$ using the absorption image acquired together with the differential phase image $I_{DP}$ can generate an image containing visible soft tissue (i.e., a bone removed image $I_A$), even if the soft tissue, such as cartilage, overlaps with the bone. The overview of this will now be described.

An absorption image is denoted by $I_{AB}$. A differential phase image, which is described above, is denoted by $I_{DP}$.

$$I_{AB} \equiv -\ln(I_{AB\_RAW}) = \int \mu \cdot dz + C \qquad \text{[Expression 1]}$$

$$I_{DP} \propto \frac{\partial}{\partial x} \int (1 - \delta) \cdot dz \qquad \text{[Expression 2]}$$

As represented by the expressions, the absorption image $I_{AB}$ can be represented as an integral of a physical quantity in the direction of X-ray irradiation (the z direction in FIG. 8), and the differential phase image $I_{DP}$ can be represented as a proportional value of a differential in a direction orthogonal to the grating structure (the y direction in FIG. 8) of the integral of a physical quantity in the direction of X-ray irradiation. $I_{AB}$_RAW denote the non-logarithmic X-ray intensity of the absorption image $I_{AB}$ reconstructed with a Talbot or Talbot-Lau interferometer. $\mu$ denotes the X-ray absorption coefficient of the subject, and $1-\delta$ denotes the X-ray refractive index of the subject. Since the relationship between $\mu$ and $\delta$ depends on the subject, differentiation of the absorption image $I_{AB}$ does not yield the differential phase image $I_{DP}$, and integration of the differential phase image $I_{DP}$ does not yield the absorption image $I_{AB}$. This phenomenon is noticed in an absorption image $I_{AB}$ and a differential phase image thereof that visualize bone but do not visualize soft tissue, such as cartilage, and a differential phase image $I_{DP}$ and an integration image thereof that visualize both bone and soft tissue. If the same structure is visualized in both the absorption image $I_{AB}$ and the differential phase image $I_{DP}$, the intensities of the signals corresponding to the common structure can be subtracted to remove the intensities of the signals corresponding to the common structure, so as to generate an image containing only structures other than the common structure. That is, even if bone overlaps with soft tissue in the differential phase image $I_{DP}$, an image that relatively clearly visualizes the soft tissue can be generated from the absorption image $I_{AB}$ and the differential phase image $I_{DP}$.

An image after removal (or subtraction) of signals corresponding to a structure common to both the absorption image $I_{AB}$ and the differential phase image $I_{DP}$ can be obtained through either of the following processes: (A) processing (differentiating) an absorption image $I_{AB}$ to generate a differential absorption image, multiplying the differential absorption image with a coefficient for matching the signal intensities of a structure common to the differential phase image $I_{DP}$ and the differential absorption image to the differential phase image $I_{DP}$, and subtracting the product from the differential phase image $I_{DP}$; or (B) processing (integrating) the differential phase image $I_{DP}$ to generate a phase image, multiplying the absorption image $I_{AB}$ with a coefficient for matching the signal intensities of the structure common to the phase image and the absorption image $I_{AB}$ to the phase image, and subtracting the product from the phase image. An image having enhanced visibility of the soft tissue through removal or subtraction of the signals corresponding to the bone through process (A) is referred to as a soft-tissue differential image. An image having enhanced visibility of the soft tissue through removal or subtraction of the signals corresponding to the bone through process (B) is referred to as a soft-tissue image. A bone removed image $I_A$ may be obtained through either process A or B. FIG. 16 illustrates an example bone removed image $I_A$ in the form of a soft-tissue differential image.

A process of generating a soft-tissue differential image, which is a bone removed image $I_A$, carried out by the controller 80 will now be described. In response to an input operation by the operator or radiologist, the controller 80 carries out the process of generating a soft-tissue differential image described below after the generation of reconstructed images, such as a differential phase image $I_{DP}$ and an absorption image $I_{AB}$, to combine a differential absorption image (not shown) obtained through processing of the absorption image and the differential phase image $I_{DP}$ (for example, see FIG. 12), so as to obtain a soft-tissue differential image.

In the process of generating a soft-tissue differential image, the absorption image $I_{AB}$ and the differential phase image $I_{DP}$ are acquired. A differential absorption image is generated from the absorption image $I_{AB}$. The differential absorption image can be acquired through differentiation of the absorption image. That is, a preferred process is, for example, generation of a differential absorption image based on the difference between adjacent pixels in the direction orthogonal to the grating structure (the y direction in FIG. 8) in the absorption image $I_{AB}$, as represented in Expressions 3.

$$dI(x,y)=I(x+1,y)-I(x-1,y) \qquad \text{[Expressions 3]}$$

dI(x,y): differential value of pixel (x,y) in x direction
I(x+1,y): pixel value of pixel (x+1,y)
I(x-1,y): pixel value of pixel (x-1,y)

Alternatively, the difference between any adjacent pixels in the absorption image $I_{AB}$ may be simply determined, or a differential filter, such as a Sobel filter, for edge detection in image processing may be used on the absorption image $I_{AB}$. Alternatively, a differential filter that has the strongest correlation between the signal shape of a differential absorption image and the signal shape of the differential phase image for a simple subject, such as a column or a sphere, may be preliminarily designed and stored, and used on the absorption image. In place of the absorption image $I_{AB}$, a non-logarithmic absorption image $I_{AB}$ corresponding to $I_{AB}$_RAW in Expression 1 may be used.

The resulting differential absorption image is multiplied by a coefficient for matching the signal intensities of the structure to be removed from the differential phase image $I_{DP}$ (the signal corresponding to bone, in this case) among the visible structures (anatomical structures) common to the differential phase image $I_{DP}$ and the differential absorption image, to the differential phase image $I_{DP}$. Specifically, the values of the pixels in the differential absorption image are multiplied by a coefficient for matching the intensities of the signals corresponding to bone to that in the differential phase image $I_{DP}$. The multiplied coefficient may be preliminarily selected in consideration of the configuration of the devices or the capturing conditions. Alternatively, the coefficient may be calculated every time. If the coefficient is to be calculated every time, the coefficient that removes the most signals corresponding to the common structure (the signals corresponding to bone) when the differential absorption image is subtracted from the differential phase image $I_{DP}$ is calculated. For example, the ratio of the signals corresponding to a common structure (signals corresponding to bone) to be removed through subtraction from the differential phase image $I_{DP}$ to the signals corresponding to the common structure in the differential absorption image is calculated, and the ratio of signals corresponding to bone in the differential phase image $I_{DP}$ to signals corresponding to bone in the differential absorption image can be calculated as the coefficient. For example, the entire image or the bone region can be selected as a region of interest, and the ratio of the pixel values in the region of interest to the pixel values in the entire region in the selected image (for example, the ratio of representative pixel values in the region of interest) can be calculated as the coefficient.

Finally, the product of the coefficient and the differential absorption image is subtracted from the differential phase image $I_{DP}$ to generate a differential phase image $I_{DP}$ from which the common structure (signals corresponding to bone) is removed or subtracted (i.e., a soft-tissue differential image). That is, values of the pixels corresponding to the differential absorption image after multiplication of the coefficient is subtracted from the values of the pixels in the differential phase image $I_{DP}$ to generate a differential phase image $I_{DP}$ from which the common structure (signals corresponding to bone) is removed or subtracted (i.e., a soft-tissue differential image). The process of generating a soft-tissue differential image can acquire a soft-tissue differential image containing visible soft tissue, even if the soft tissue overlaps with the bone in the captured image.

In the time between the Talbot capturing device 61 capturing an image containing a subject and an image not containing the subject, the positions of the gratings may slightly shift due to a temperature variation or heat. The slight shifting of the positions of the gratings has substantially no influence on the absorption image $I_{AB}$ but causes an artifact, such as a gradient in signals, on the plane of the differential phase image $I_{DP}$. In such a case, an appropriate coefficient for multiplication with the differential absorption image may not be determined through calculation. The artifact in the differential phase image $I_{DP}$ caused by the positional shift of the gratings can be approximated with a primary or secondary function of two-dimensional coordinates (x,y) on the image. Thus, as disclosed in Japanese Patent Application No. 2011-035593, for example, a coefficient of the function that recreates the most accurate artifact component can be estimated and subtracted from the differential phase image $I_{DP}$, to correct the signals corresponding to the artifact. Thus, it is preferred that the controller 80 receives the differential phase image $I_{DP}$, carries out the artifact correction, and generates a soft-tissue differential image from the artifact-corrected differential phase image $I_{DP}$ and the absorption image $I_{AB}$. Alternatively, a fluctuation in the signal caused by factors other than the subject may be removed from the signal distributions of the differential phase image $I_{DP}$ and the differential absorption image to generate a soft-tissue differential image.

In the process of generating a soft-tissue differential image described above, an image acquired through multiplication of a differential absorption image with a constant coefficient is subtracted from the differential phase image $I_{DP}$. A differential phase image $I_{DP}$ capturing a joint region as the subject contains signals of sufficient intensity corresponding to the soft tissue in the region without overlap of soft tissue and bone. If a differential absorption image is subtracted from such a region, the noise component is enhanced and may cause a reduction in image quality. Thus, it is preferable to determine the bone region in the differential absorption image and multiply a smaller coefficient with the other regions in the differential absorption image. This can prevent a reduction in image quality.

A bone region can be determined by preliminarily storing a threshold for the absorption image in a storage unit, and comparing the pixel values in the absorption image $I_{AB}$ and the threshold to determine the region satisfying the following expression as a bone region:

$$\text{Pixel value of absorption image } I_{AB} > \text{threshold} \quad (1)$$

The absorption image $I_{AB}$ is defined by Expression 1 (the region having high absorption due to the subject has a large pixel value). Thus, the threshold defines the upper limit of the values of pixels in the region other than bone. If the regions having low absorption due to the subject has large pixel values, a threshold defining the lower limit of the values of the pixels in the region other than bone is stored in the storage unit. Any region that falls below the threshold defining the lower limit (having a pixel value below the threshold defining the lower limit) is determined as the bone region.

Alternatively, the threshold corresponding to the differential absorption image may be preliminarily stored in the storage unit, and the absolute values of the pixel values in the differential absorption image may be compared with the threshold of the differential absorption image stored in the storage unit to determine the region satisfying the following expression as the bone region:

$$\text{Absolute value of pixel value of differential absorption image} > \text{threshold} \quad (2)$$

Alternatively, the threshold for the small-angle scattering image $I_V$ may be stored in the storage unit, and the pixel values of the small-angle scattering image $I_V$ may be compared with the threshold to determine the region satisfying the following expression as the bone region:

$$\text{Pixel value of small-angle scattering image } I_V > \text{threshold} \quad (3)$$

Alternatively, the threshold for the phase image (i.e., image generated through processing (integration) of the differential phase image $I_{DP}$, as described above) may be stored in the storage unit, and the pixel values of the phase image may be compared with the threshold to determine the region satisfying the following expression as the bone region:

$$\text{Pixel value of phase image} > \text{threshold} \quad (4)$$

Similarly, the threshold for the differential phase image $I_{DP}$ may be stored in the storage unit, and the absolute values of the pixel values of the differential phase image $I_{DP}$ may be compared with the threshold of the differential phase image $I_{DP}$ stored in the storage unit to determine the region satisfying the following expression as the bone region:

$$\text{Absolute value of pixel value of differential phase image } I_{DP} > \text{threshold} \quad (5)$$

Upon completion of the generation of a bone removed image, such as a soft-tissue differential image, the controller 80 displays the bone removed image $I_A$ (i.e., soft-tissue differential image (see FIG. 16)) generated as described above in the form of a combined image of the differential phase image $I_{DP}$ and the absorption image $I_{AB}$, for example, on the display 80a. For example, the soft-tissue differential image described above is an image obtained through removal or subtraction of signals corresponding to bone in the differential phase image $I_{DP}$, which visualizes signals corresponding to both bone and soft tissue, such as cartilage. Thus, a medical doctor can visibly confirm the signals corresponding to soft tissue in a displayed soft-tissue differential image, even if the image contains overlapping bone and soft tissue.

For example, a GUI, including buttons and slide bars, is displayed on the control panel CP (see FIG. 16) so that the controller 80 can be operated to vary the levels of contribution of the differential phase image $I_{DP}$ and the differential absorption image in the generation of a bone removed image, such as a soft-tissue differential image. Alternatively, a GUI may be provided to independently vary the level of contribution of the images to the bone region and the level of contribution of the images to regions other than bone. In response to an instruction through operation of the control panel CP to vary the level of contribution, the controller 80 calculates a coefficient in accordance with the level of contribution instructed through the control panel CP, multiplies the coefficient with the differential absorption image, subtracts the product from the differential phase image $I_{DP}$, and displays a combined image (i.e., soft-tissue differential image) having a varied level of contribution. This allows a medical doctor to manually and freely vary the levels of contribution of the differential phase image $I_{DP}$ and the differential absorption image. In this way, for example, a small coefficient can be multiplied with a differential absorption image so as to visualize both bone and soft tissue for determination of the position of the soft tissue. Alternatively, the coefficient can be increased to enhance the descriptiveness of soft-tissue. Thus, diagnosis of soft tissue can be facilitated.

[Rotation of Image for Display]

Figure 17A:
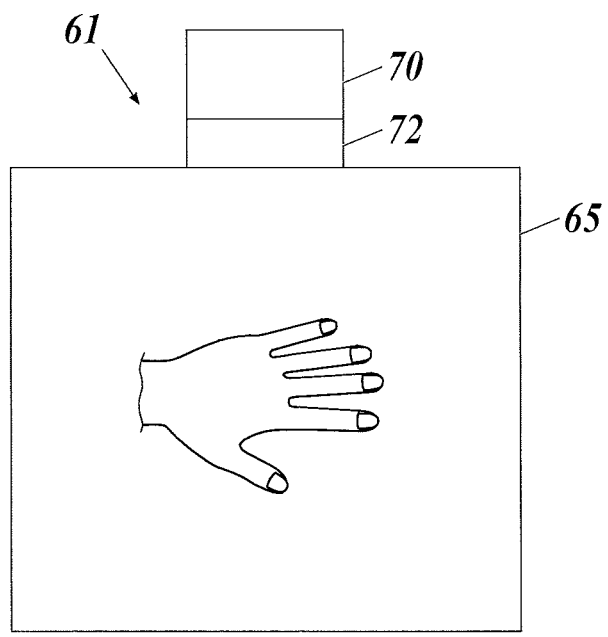
FIG. 17A illustrates a process of capturing a hand of a patient sitting to the left of the Talbot capturing device while extending the hand on a subject table.
Figure 17B:
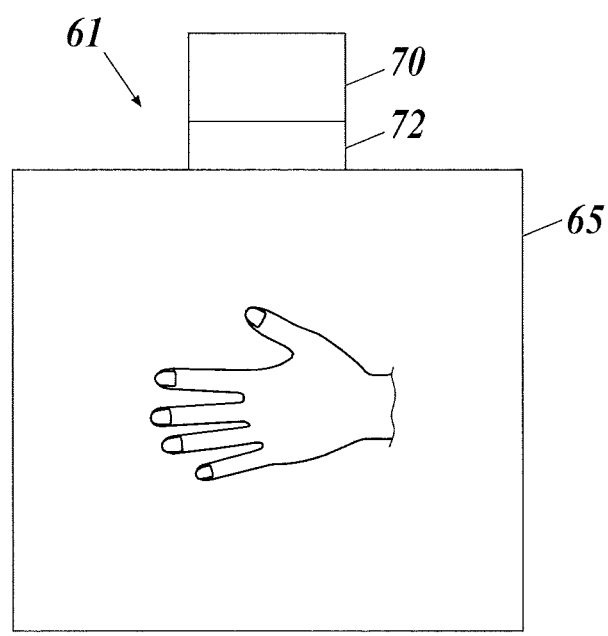
FIG. 17B illustrates a process of capturing a hand of a patient sitting to the right of the Talbot capturing device while extending the hand on a subject table.

The process of displaying general images including small-angle scattering images $I_V$ and $I_V^*$ on the display 80a of the controller 80 will now be described. For example, FIG. 12 illustrates an image of the joint region in a hand disposed such that the direction of the bones (the extending direction of the bones) is horizontal in the image. This indicates that the hand of the patient who is the subject is fixed on the subject table 65 of the Talbot capturing device 61 during capturing as illustrated in FIG. 17A in view from the side of the Talbot capturing device 61 adjacent to the X-ray source 62 (see FIG. 8) (i.e., viewing downward from the top of the device). That is, with reference to FIG. 17A, when the side where the supporting column 70 of the Talbot capturing device 61 is provided is to be the far side, capturing of a hand of a patient is performed while the patient (not shown) sits to the left of the Talbot capturing device 61, and extends his or her hand over the subject table 65. The fastening device is omitted in FIGS. 17A and 17B. FIGS. 17A and 17B illustrate the capturing of a left hand of the patient. Capturing of the right hand is also performed through the same procedures.

With reference to FIG. 17B, if a patient (not shown) sits to the right of the Talbot capturing device 61 and extends his or her hand over the subject table 65, the orientation (extending direction) of the joint region in the captured image is opposite to that in FIG. 17B. That is, in FIG. 17A, the tips of the fingers of the patient face to the right, whereas in FIG. 17B, the tips of the fingers face to the left. For example, the orientation of a knee joint of a patient in an image captured while the patient sits to the left of the Talbot capturing device 61 and extends his or her leg over the subject table 65 is opposite to that of the patient sitting to the right. If the orientation of the joint region varies in every image in this way, a medical doctor might mistake right for left or vice versa when observing images of hands and legs for diagnosis.

For example, images of a hand and a leg of a patient of interest can be rotated by 90° or 270° such that the fingers face upward in the image and the tip of the leg faces downward in the image. In this way, a medical doctor can observe images of joints in hands and legs always in the same orientation and make correct diagnoses.

For capturing in a medical facility, for example, the patient can be preliminarily determined to sit to the left of the Talbot capturing device 61 (such as in FIG. 17A) or to the right (such as in FIG. 17B). In this way, the controller 80 should simply rotate the image by 90° or 270° for display, and the processing load is reduced. Alternatively, if the operator or radiologist determines which side of the Talbot capturing device 61 the patient sits for capturing, the position of the patient is not preliminarily determined. In such a case, the controller 80 may analyze the reconstructed image which is reconstructed and generated and determine the rotation (90° or 270°) of the image to be displayed.

Alternatively, the Talbot capturing device 61 in a default state may be automatically rotated to display images of a hand and a leg of a patient of interest such that the fingers face upward in the image and the tip of the leg faces downward in the image. Alternatively, the operator or radiologist may instruct the Talbot capturing device 61 not to automatically rotate the images. The Talbot capturing device 61, i.e., an X-ray capturing device including a Talbot or Talbot-Lau interferometer or an X-ray capturing device involving Fourier transform, can generate not only a conventional absorption image $I_{AB}$, but also a differential phase image $I_{DP}$, a small-angle scattering image $I_V$, and an image combining these reconstructed images.

The inventors have found that when a differential phase image $I_{DP}$ captured by the Talbot capturing device 61 is displayed on the display 80a of the controller 80, the colors black and white are inverted (i.e., the signal values for the pixels are inverted for black and white) in the generated differential phase image $I_{DP}$ capturing a hand placed on the subject table 65 as illustrated in FIG. 17A (hereinafter this orientation is referred to as position L because capturing is performed with the patient extending his or her hand or leg over the subject table 65 while sitting to the left of the Talbot capturing device 61) and the differential phase image $I_{DP}$ capturing the hand placed as illustrated in FIG. 17B (similarly, hereinafter this orientation is referred to as position R). This is due to difference in differential direction.

For example, based on such finding, in an embodiment described above, the controller 80 can carry out image processing to invert the signals received during capturing in the L direction to match an image captured in the R direction (or vice versa). In such a case, each medical facility can determine either L or R as the standard.

In other words, the finding described above has achieved the advantage of determining the L direction (for example, see FIG. 17A) or the R direction (for example, see FIG. 17B) of a differential phase image $I_{DP}$ on the basis of the condition of the signals (i.e., normal black and white or inverted black and white), thereby determining the right and left of the captured site (i.e., right or left hand (leg)). The controller 80 can also be configured to determine right and left as described above.

Figure 18A:
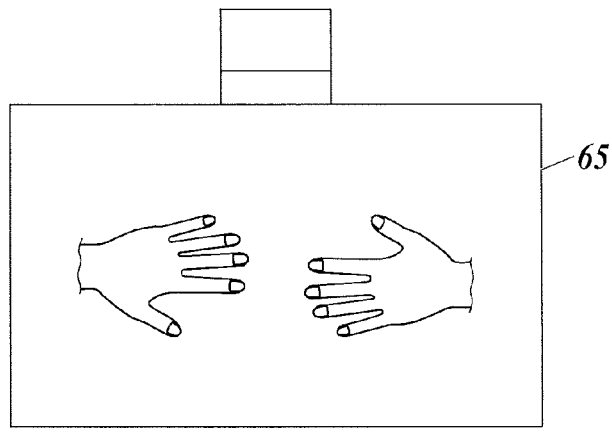
FIG. 18A illustrates hands can be disposed on the subject table in various directions when a two-dimensional grating is used.
Figure 18B:
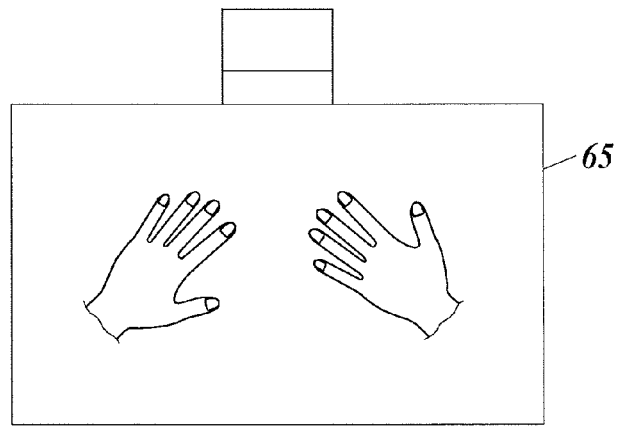
FIG. 18B illustrates the hands can be disposed on the subject table in various directions when a two-dimensional grating is used.
Figure 18C:
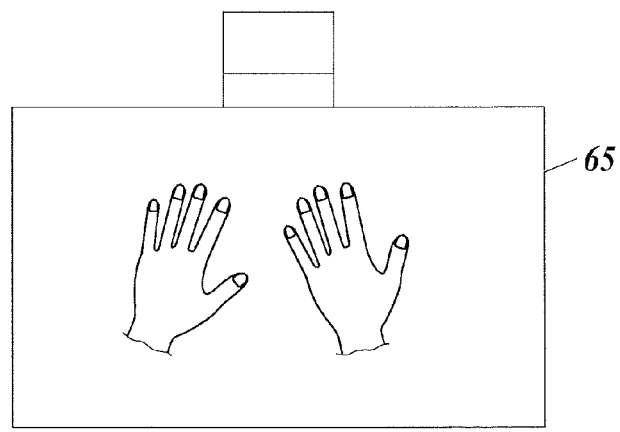
FIG. 18C illustrates the hands can be disposed on the subject table in various directions when a two-dimensional grating is used.

The Talbot capturing device according to Japanese Patent Application Laid-Open No. 2012-78350 including a grating having two-dimensional bright sections (hereinafter, referred to as two-dimensional grating) and involving Fourier transform can also determine right and left. A Talbot capturing device 61 according to an embodiment described above including one-dimensional gratings having slits (see FIG. 9), such as the first grating 66 and the second grating 67 (see FIG. 8), captures an image of a hand of a patient of interest extended over the subject table 65 from the left (L direction) or the right (R direction) of the Talbot capturing device 61, as illustrated in FIGS. 17A and 17B, respectively. A Talbot capturing device 61 including two-dimensional gratings can capture images of a hand extended over the subject table 65 from various directions, as illustrated in FIGS. 18A, 18B, and 18C, for example. FIGS. 18A to 18C illustrate the various directions a hand on the subject table 65 can be placed when two-dimensional gratings are used and do not illustrate the hands of two patients or both hands of one patient placed at the same time on the subject table 65. That is, for example, FIGS. 17A and 17B are combined into a single drawing in FIG. 18A.

Similar to the description above, when two-dimensional gratings are used, the controller 80 can carry out image processing to invert signals captured in the L direction to match an image captured in the R direction (or vice versa), or otherwise the right and left of the captured site may be determined. If two-dimensional gratings are used, there is a difference in the visibility of the inverted signals. For example, with reference to FIGS. 18A to 18C, the visibility of the inverted signals is the highest in FIG. 18A, and decreases sequentially from FIG. 18B to FIG. 18C. The determination of the left and right of the captured site is important information associated with the treatment and therapy to be performed on the affected site in the hand or leg of the patient and should not be mistaken. For example, detection information on the positioning of the fastening device and analytical information on inversion of black and white can be used together to enhance the accuracy of visibility of inverted signals.

The embodiment and modifications described above should not be construed to limit the present invention and may be modified in various ways within the scope of the present invention.

INDUSTRIAL APPLICABILITY

The system of the present invention can be used in fields of radiation image capturing (medical fields in particular).

The invention claimed is:

1. A diagnostic medical image system comprising:
    a first capturing unit comprising:
        an X-ray source which irradiates X-ray beams; and
        an X-ray capturing device which reads the X-ray beam irradiated from the X-ray source and passing through a subject as an image signal, the first capturing unit reading the image signal corresponding to one image generated at the X-ray capturing device through one irradiation operation of the X-ray capturing device with the X-ray beam irradiated from the X-ray source and passing through the subject;
    a console which receives the image signal corresponding to one image from the first capturing unit, generates one diagnostic medical image from the received image signal corresponding to one image, and links the one generated diagnostic medical image to one corresponding capturing order information;
    a second capturing unit comprising:
        an X-ray source;
        a plurality of gratings; and
        an X-ray detector which includes a two-dimensional array of transducers generating electrical signals in response to the X-ray beams irradiated from the X-ray source and passing through the subject and the plurality of gratings and reads the electrical signals generated at the transducers as image signals, the second capturing unit reading the image signals corresponding to multiple images generated at the X-ray detector through multiple irradiation operations of the X-ray detector with the X-ray beams irradiated from the X-ray source and passing through the subject and the plurality of gratings; and
    a controller which reconstructs and generates several types of diagnostic medical images from the image signals corresponding to multiple images read by the second capturing unit, wherein,
    the controller consolidates the generated several types of diagnostic medical images and sends the consolidated diagnostic medical images to the console; and
    the console links the consolidated several types of diagnostic medical images sent from the controller to one corresponding capturing order information, through a process identical to the process of linking the one diagnostic medical image captured by the first capturing unit to one capturing order information.

2. The diagnostic medical image system according to claim 1, wherein,
    the console includes a selection unit to select the first capturing unit or the second capturing unit, wherein
    if the first capturing unit is selected, upon receiving the image signal corresponding to one image from the first capturing unit, the console generates the diagnostic medical image from the image signal corresponding to one image and links the diagnostic medical image to the corresponding capturing order information,
    if the second capturing unit is selected, upon receiving the consolidated several types of diagnostic medical images from the controller, the console collectively links the consolidated several types of diagnostic medical images to the one capturing order information.

3. The diagnostic medical image system according to claim 1, further comprising:
    at least one capturing room,
    wherein, the controller is installed in each capturing room provided with the second capturing unit.

4. The diagnostic medical image system according to claim 1, wherein,
    the controller is composed of a portable terminal, and
    the controller receives the image signals corresponding to multiple images from the second capturing unit via wireless communication, generates several types of diagnostic medical images from the image signals corresponding to multiple images, consolidates the generated several types of diagnostic medical images, and sends the consolidated diagnostic medical images to the console via wireless communication.

5. The diagnostic medical image system according to claim 1, wherein,
the controller reconstructs and generates the several types of diagnostic medical images from the image signals corresponding to multiple images read at the second capturing unit with at least two modes, a normal mode for generating diagnostic medical images having a normal gradation and a high-gradation mode for generating diagnostic medical images in a higher gradation, and
the controller consolidates the several types of diagnostic medical images generated with at least the normal mode and sends the consolidated diagnostic medical images to the console.

6. The diagnostic medical image system according to claim 5, wherein the controller consolidates the several types of diagnostic medical images generated in the high-gradation mode and sends the consolidated diagnostic medical images to the console.

7. The diagnostic medical image system according to claim 5, wherein the several types of diagnostic medical images generated in the high-gradation mode are output to a predetermined storage medium.

8. The diagnostic medical image system according to claim 1, wherein,
instead of the controller reconstructing and generating several types of diagnostic medical images from the image signals corresponding to multiple images read by the second capturing unit, and consolidating and sending the generated several types of diagnostic medical images to the console, and the console linking the consolidated several types of diagnostic medical images sent from the controller to one corresponding capturing order information, through a process identical to the process of linking the one diagnostic medical image captured by the first capturing unit to one piece of capturing order information,
the controller consolidates the image signals corresponding to multiple images read by the second capturing unit and sends the consolidated image signals to the console, and
upon receiving the image signal corresponding to one image from the first capturing unit, the console generates one diagnostic medical image from the received image signal corresponding to one image, and links the generated diagnostic medical image to one corresponding capturing order information, or upon receiving the consolidated image signals corresponding to multiple images from the controller, the console reconstructs and generates several types of diagnostic medical images from the image signals corresponding to multiple images, and links the generated several types of diagnostic medical images to one corresponding capturing order information.

9. The diagnostic medical image system according to claim 8, wherein the controller consolidates image signals corresponding to multiple background images captured by background capturing in which capturing is performed by the second capturing unit through irradiation of X-ray beams irradiated from the X-ray source without a subject, and sends the consolidated image signals to the console.

10. The diagnostic medical image system according to claim 1, wherein the controller or the console first displays a small-angle scattering image among the several types of diagnostic medical images on a display.

11. The diagnostic medical image system according to claim 10, wherein the controller or the console generates a decimated moire image by decimating pixels in the image signals corresponding to multiple images read by the second capturing unit, and first reconstructs and generates the small-angle scattering image from the generated decimated moire image.

12. The diagnostic medical image system according to claim 11, wherein the controller or the console generates the several types of diagnostic medical images from the image signals corresponding to multiple images without decimation, while generating and displaying the small-angle scattering image from the decimated moire image.

13. The diagnostic medical image system according to claim 12, wherein the controller or the console cancels generation of the several types of diagnostic medical images from the image signals corresponding to the undecimated multiple images if recapturing is instructed.

14. A method of introducing a Talbot capturing device to a diagnostic medical image system for general capturing comprising an X-ray source which irradiates X-ray beams, an X-ray capturing device which reads the X-ray beams irradiated from the X-ray source and passing through a subject as image signals, and a console which links one diagnostic medical image generated from the image signal corresponding to one image received from the X-ray capturing device to one corresponding capturing order information, the X-ray capturing device reading the image signal corresponding to one image through one irradiation operation of the X-ray capturing device with the X-ray beams irradiated from the X-ray source and passing through a subject, the method comprising:
introducing the Talbot capturing device comprising an X-ray source, a plurality of gratings, and an X-ray detector which includes a two-dimensional array of transducers generating electrical signals in response to the X-ray beams irradiated from the X-ray source and passing through the subject and the plurality of gratings and reads the electrical signals generated at the transducers as image signals, the X-ray detector reading the image signal corresponding to one image through one irradiation operation of the X-ray detector with the X-ray beams irradiated from the X-ray source and passing through the subject and the gratings; and
operating the console to reconstruct and generate several types of medical images from the image signal corresponding to one image, to consolidate the generated several types of medical images, and to link the generated several types of medical images to one corresponding capturing order information, upon reception of the image signal corresponding to one image from the Talbot capturing device.

15. A method of introducing a Talbot capturing device to a diagnostic medical image system for general capturing comprising an X-ray source which irradiates X-ray beams, an X-ray capturing device which reads the X-ray beams irradiated from the X-ray source and passing through a subject as image signals, and a console which links one diagnostic medical image generated from the image signal corresponding to one image received from the X-ray capturing device to one corresponding capturing order information, the X-ray capturing device reading the image signal corresponding to one image through one irradiation operation of the X-ray capturing device with the X-ray beams irradiated from the X-ray source and passing through a subject, the method comprising:

introducing the Talbot capturing device comprising an X-ray source, a plurality of gratings, and an X-ray detector which includes a two-dimensional array of transducers generating electrical signals in response to the X-ray beams irradiated from the X-ray source and passing through the subject and the plurality of gratings and reads the electrical signals generated at the transducers as image signals, the X-ray detector reading the image signal corresponding to one image through one irradiation operation of the X-ray detector with the X-ray beams irradiated from the X-ray source and passing through the subject and the gratings;

consolidating the generated several types of diagnostic medical images and sending the consolidated diagnostic medical images to the console with a controller which reconstructs and generates several types of diagnostic medical images from the image signal corresponding to one image received from the Talbot capturing device; and operating the console to link the consolidated several types of diagnostic medical images sent from the controller to one corresponding capturing order information.

* * * * *